US005277175A

United States Patent [19]

Riggs et al.

[11] Patent Number: 5,277,175
[45] Date of Patent: Jan. 11, 1994

[54] CONTINUOUS FLOW NEBULIZER APPARATUS AND METHOD, HAVING MEANS MAINTAINING A CONSTANT-LEVEL RESERVOIR

[76] Inventors: John H. Riggs, 3720 Summer Pl., Raleigh, N.C. 27604; Barry Mangum, 1105 Shadywood La., Raleigh, N.C. 27603

[21] Appl. No.: 729,518

[22] Filed: Jul. 12, 1991

[51] Int. Cl.[5] .................... A61M 11/00; A61M 16/10; A61M 15/00; B05B 7/00

[52] U.S. Cl. .......................... 128/200.21; 128/203.12; 128/204.21; 128/200.19; 128/203.14

[58] Field of Search ...................... 128/200.19, 200.14, 128/200.21, 200.18, 203.12, 203.19, 203.21, 203.24, 203.25, 203.29, 204.21, 204.23, 204.26, 203.14, 200.16; 73/149, 290 R, 293; 239/305, 338; 604/31, 65-67; 80, 81, 246, 251, 255, 257, 258, 260, 262; 137/256

[56] References Cited

U.S. PATENT DOCUMENTS

| | | | |
|---|---|---|---|
| 3,172,406 | 3/1965 | Bird . | |
| 3,185,179 | 5/1965 | Harautuneian | 137/625.47 |
| 3,232,292 | 2/1966 | Schaefer . | |
| 3,387,607 | 6/1968 | Gauthier et al. | 128/200.16 |
| 3,593,712 | 7/1971 | Weaver et al. | 128/200.16 |
| 3,746,000 | 7/1973 | Edwards | 128/200.16 |
| 3,809,080 | 5/1974 | Deaton . | |
| 3,864,326 | 2/1975 | Babington . | |
| 3,874,379 | 4/1975 | Enfield et al. . | |
| 3,990,442 | 11/1976 | Patneau . | |
| 4,086,765 | 2/1978 | Levine . | |
| 4,094,318 | 6/1978 | Burke et al. | 604/81 |
| 4,098,853 | 7/1978 | Brown et al. | 128/200.13 |
| 4,195,044 | 3/1980 | Miller | 128/200.21 |
| 4,197,843 | 4/1980 | Bird | 128/200.14 |
| 4,253,501 | 3/1981 | Ogle | 141/27 |
| 4,275,726 | 6/1981 | Schael | 604/31 |
| 4,301,970 | 11/1981 | Craighero | 239/338 |
| 4,366,105 | 12/1982 | Nowacki | 261/35 |
| 4,462,397 | 7/1984 | Suzuki . | |
| 4,509,943 | 4/1985 | Hanzawa | 604/31 |
| 4,541,966 | 9/1985 | Smith | 128/200.21 |

(List continued on next page.)

FOREIGN PATENT DOCUMENTS

| | | | |
|---|---|---|---|
| 58945 | 2/1938 | Norway . | |
| 2164569 | 3/1986 | United Kingdom | 128/200.21 |
| 8606969 | 12/1986 | World Int. Prop. O. | 128/200.21 |

OTHER PUBLICATIONS

McPherson, "Respiratory Therapy Equipment", The C. V. Mosby Co., 1981, pp. 149-153. ISBN 0-8016-33-13-3.

(List continued on next page.)

*Primary Examiner*—Edgar S. Burr
*Assistant Examiner*—Kimberly L. Asher
*Attorney, Agent, or Firm*—Steven J. Hultquist

[57] ABSTRACT

A continuous flow nebulizing device for patients receiving long term nebulized medicant respiratory therapy. The nebulizing device comprises a nebulizer vial through which nebulizing fluids are delivered from a large supply vessel to conventional nebulizing apparatus. Thereby, the nebulizing apparatus connected to the continuously replenished nebulizer vial, delivers a larger volume of nebulized medicants on a continuous basis to a patient than can be provided by a conventional nebulizer vial without removing the conventional nebulizer vial from the nebulizer. For critially ill patients, the nebulizing device is used as part of a nebulizer/ventilator circuit. For voluntary respiratory patients, the nebulizer device output is used without a ventilator. Medicant supplying circuits are provided whereby a single medicant is selectably delivered from a plurality of large supply vessels without disconnecting the nebulizing vial from the nebulizer. Liquid level control circuits are provided whereby the level of liquid in the nebulizer vial is electrically or fluidically controlled. Nebulizing gas flow, synchronized with inhalation and exhalation rates, provides a plurality of options of aerosolized mist production patterns. Such synchronization is defined by a ventilator. An add-site device which provides direct access by a syringe needle into the nebulizer vial for addition of medicants and withdrawal of fluid is disclosed. Adjustable temperature control is provided for ventilating and nebulizeable fluids.

15 Claims, 11 Drawing Sheets

U.S. PATENT DOCUMENTS

| | | | |
|---|---|---|---|
| 4,546,794 | 10/1985 | Ball | 128/200.19 |
| 4,657,007 | 4/1987 | Carlin et al. | |
| 4,682,010 | 7/1987 | Drapeau et al. | 128/204.17 |
| 4,805,609 | 2/1989 | Roberts et al. | 128/200.21 |
| 4,832,012 | 5/1989 | Raabe et al. | 128/200.21 |
| 4,832,012 | 5/1989 | Raab et al. | |
| 4,838,856 | 6/1989 | Mulreany et al. | 604/81 |
| 4,920,336 | 4/1990 | Meijer | |
| 4,921,642 | 5/1990 | LaTorraca | 128/203.27 |
| 4,938,209 | 7/1990 | Fry | 128/200.21 |
| 4,946,439 | 8/1990 | Eggers | 604/81 |
| 4,950,245 | 8/1990 | Brown et al. | 604/67 |
| 4,951,661 | 8/1990 | Sladek | 128/202.27 |
| 5,025,829 | 6/1991 | Edwards et al. | 604/247 |
| 5,080,093 | 1/1992 | Raabe et al. | 128/200.21 |
| 5,119,807 | 6/1992 | Roberts et al. | 128/200.21 |

OTHER PUBLICATIONS

Patent Application Abstract of the Invention, Nov. 4, 1989.

Magazine article, Vortran Medical technology, Inc.

Undated newspaper article, Associated Press, Lung Drug May Help Treat AIDS.

Bradley Chipps, M.D., Aerosol Therapy for Continuous Brochodilation, Updates in Cardio-Pulmonary Medicine, Nov. 16, 1989.

News Release dated Aug., 1990 Lung Surfactant Replacement Therapy Jay Portnoy, M.D. and Jag Aggarwal, M.D., Continuous Terbutaline Nebulization for the Treatment of Severe Exacerbations of Asthma in Children, Annals of Allergy.

Special Report by Alan C. Jasper, Md., Stanley Kahan, M.D., and Spencer K. Koerner, M.D., Cost-Benefit Comparison of Aerosol Bronchodilator Delivery Methods in Hospitalized Patients.

Neo Fax, Exosurf, dated Oct. 1990.

Magazine article by W. Seeger, U. Pison, R. Buchhorn, U. Obertacke, and T. Joka, Surfactant Abnormalities and Adult Respiratory Failure, Lung (1990).

Medisonic Respiratory Care Products, Medisonic "In--line" Medical Drug Dispenser.

The New England Journal of Medicine, No. 12, dated Sep. 20, 1990, Aerosolized Pentamidine for Prophylaxis Against Pneumocystis Carinii Pheumonia.

Description of a Delivery Method for Continuously Aerosolized Albuterol in Status Asthmaticus by Karen R. Voss, CRTT, Sandra K. Willsie-Ediger, D.O., Dennis R. Pyszczynski, M.D., FCCP.

Article: An Apparatus for Continuous Aerosol Administration Article by Jay K. Kolls, M.D., Robert C. Beckerman, M.D., and Bettina Hilman, M.D.: Comparison of Continuous vs. Frequent Intermittent Aerosolized Albuterol in Status Asthmaticus.

Article by H. William Kelly, Bennie C. McWilliams, M.D., Robert Katz, M.D., and Shirley Murphy, M.D.: Safety of Frequent High Dose Nebulized Terbutaline in Children With Acute Severe Asthma.

The Management of Acute Exacerbation of Childhood Asthma.

Article by Antoinette Colacone, Normon Wolkova, M.D., FCCP, Errol Stern, M.D., Marc Afilalo, M.D., Thomas M. Rosenthal, M.D., and Harvey Kreisman, M.D., FCCP, Continuous Nebulization of Albuterol in Acute Asthma.

Videotape, Aerosol Delivery of Exosurf, 19:15 (VHS).

Article by M. Ba, et al., Effects of Continuous Inhalation of Salbutamol (s) in Acute Asthma.

Article by F. W. Moler, et al., Improvement of Clinical Asthma Score and PaCo2 in Children with Severe Asthma Treated with Continuously Nebulized Terbutaline.

Medisonic Respiratory Fine Humidifier.

Medisonic Spiral 3612 Portable Ultra-Sonic Drug Inhaler.

Medisonic Compact HF-31 Humidifier/Inhaler.

Medisonic Minimax-Ultra-sonic Medication Inhaler.

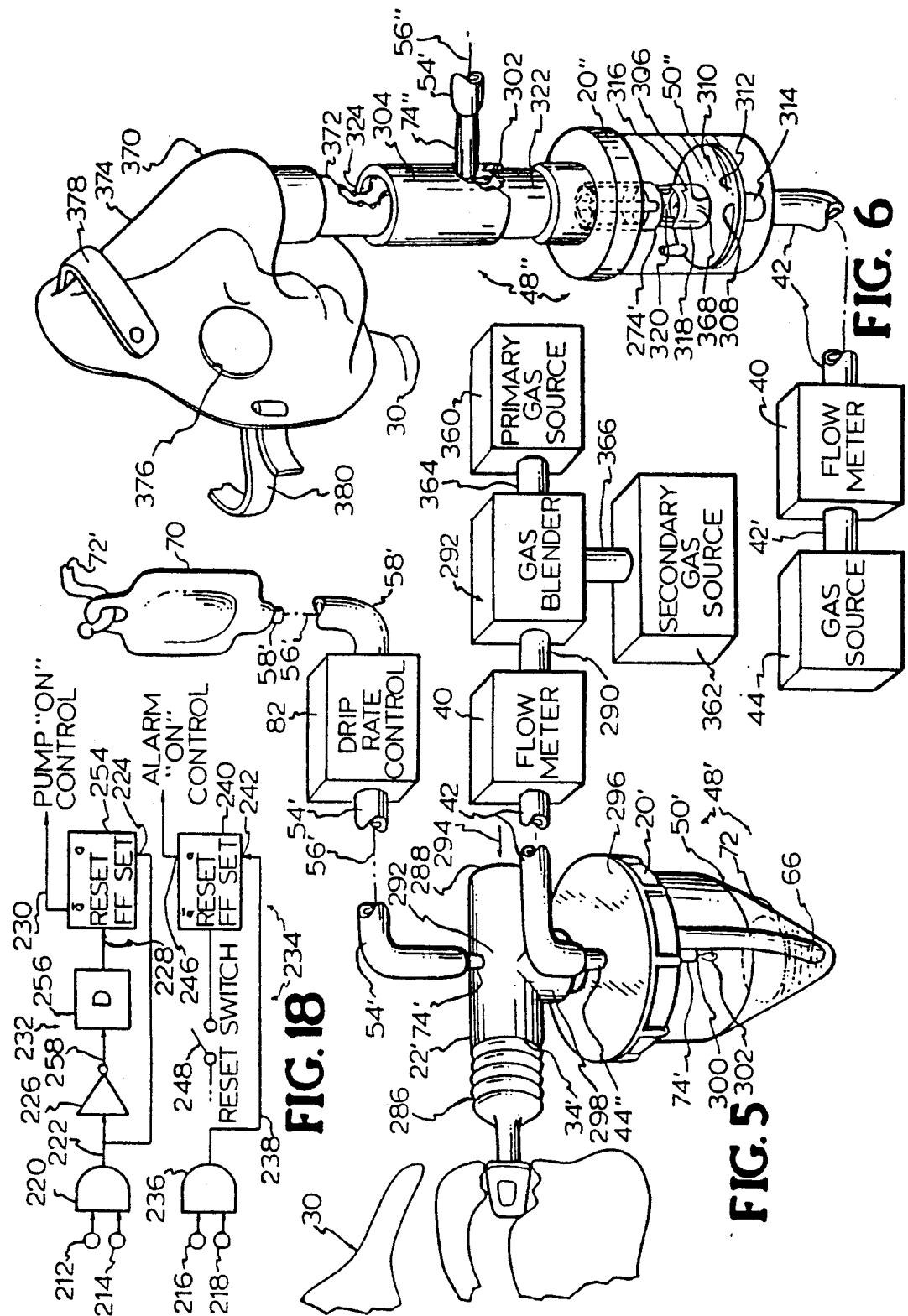

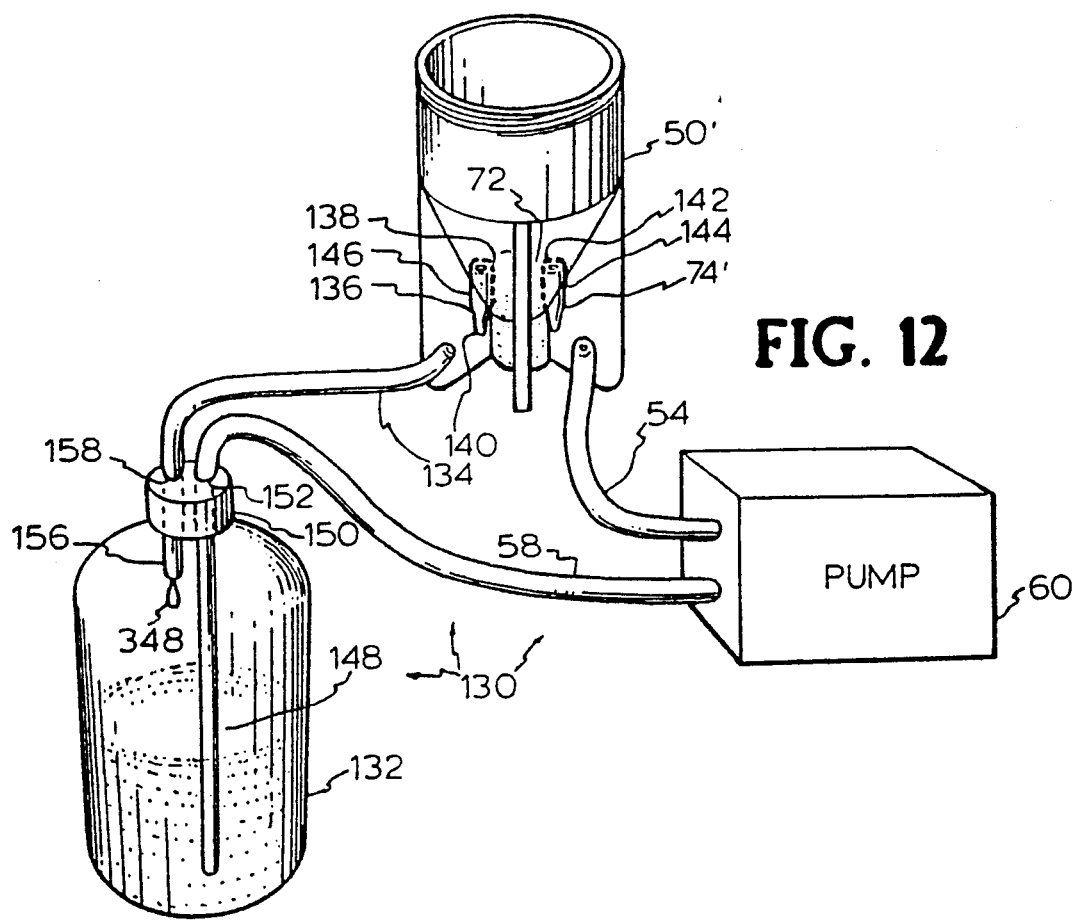

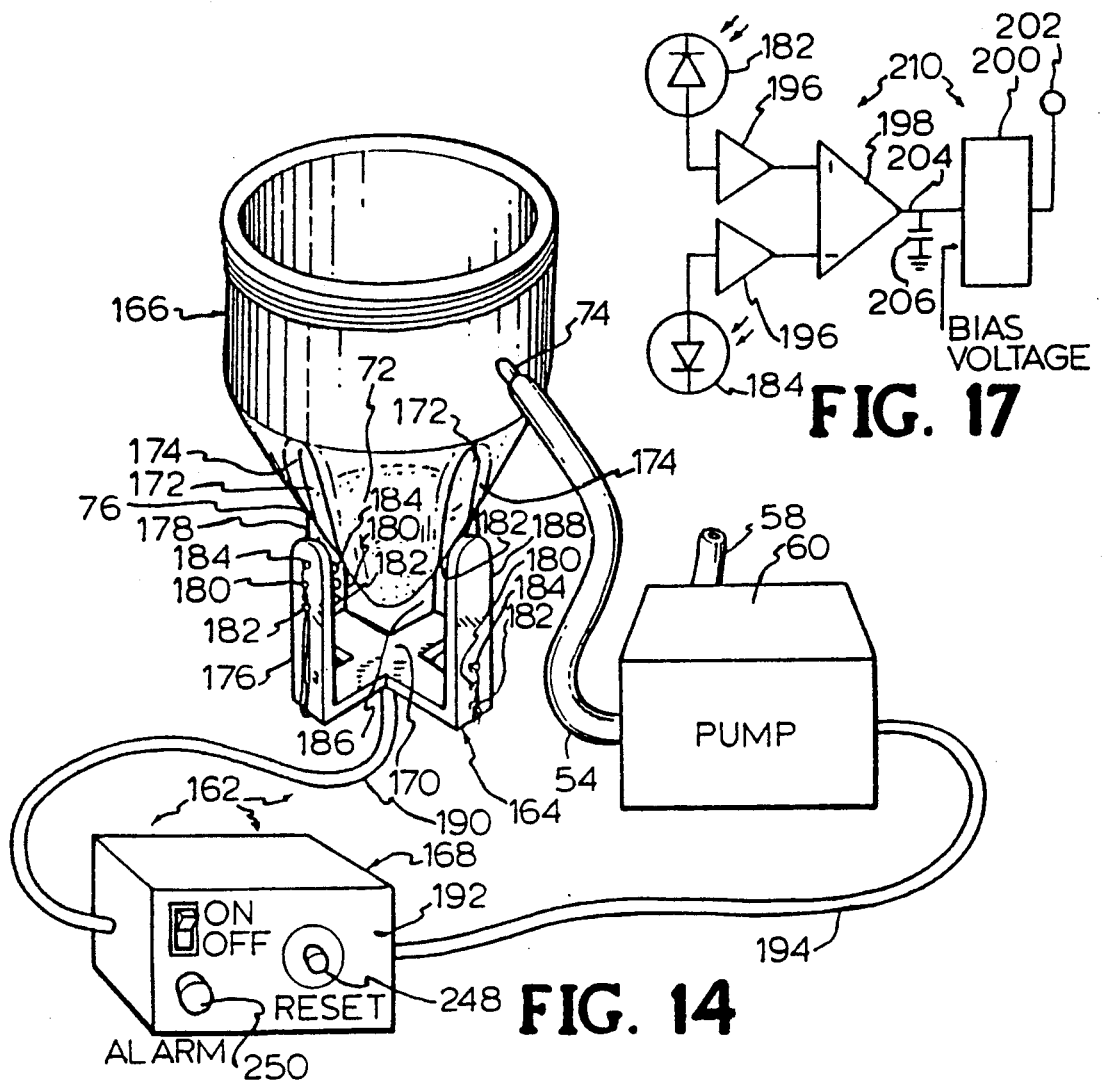
FIG. 17
FIG. 14
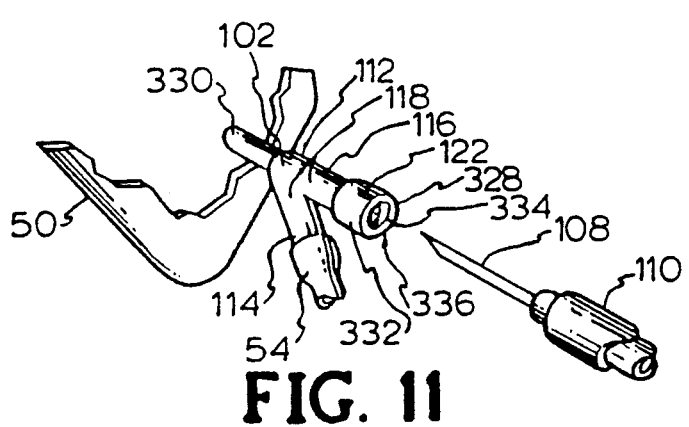
FIG. 11

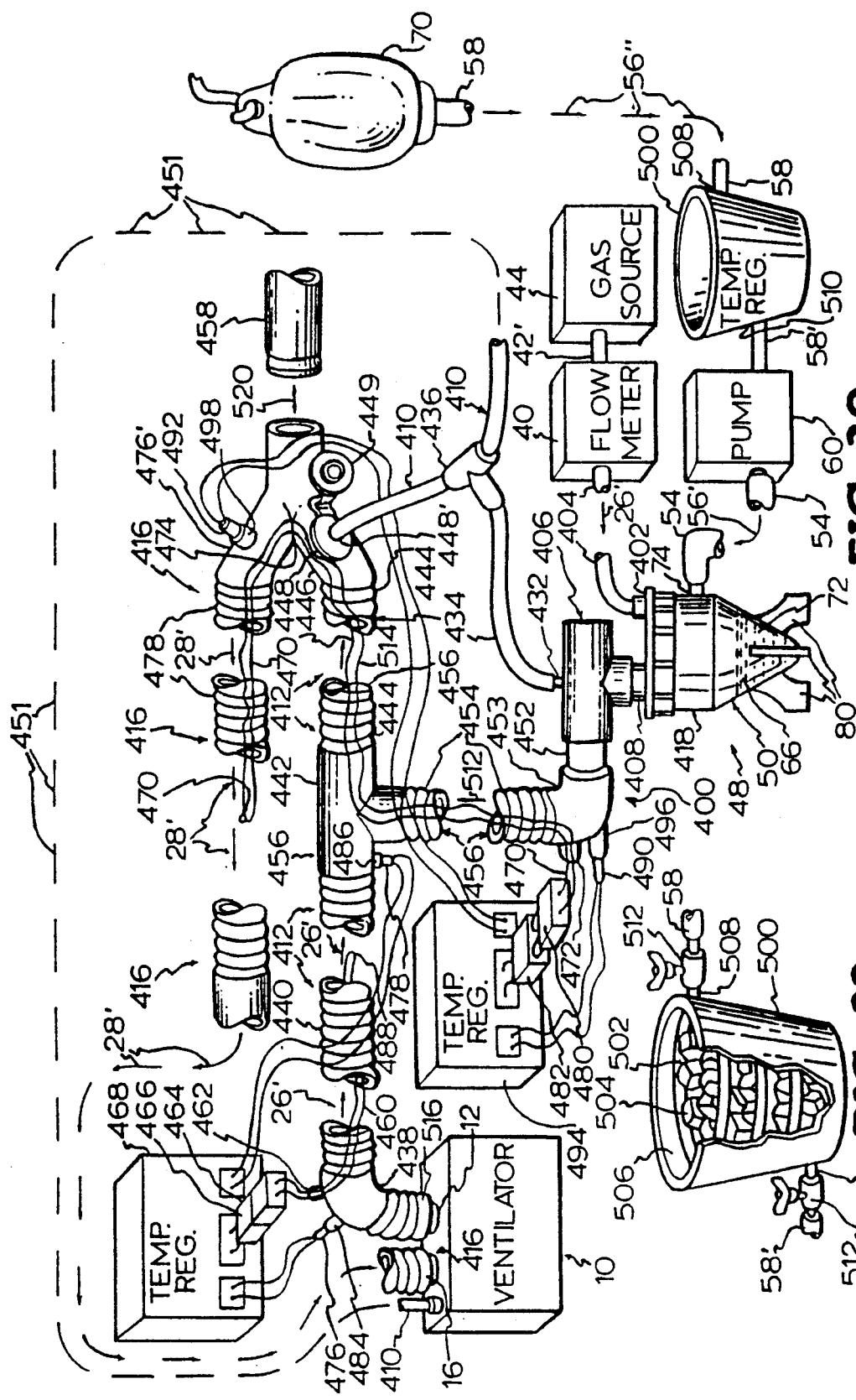

CONTINUOUS FLOW NEBULIZER APPARATUS AND METHOD, HAVING MEANS MAINTAINING A CONSTANT-LEVEL RESERVOIR

FIELD OF INVENTION

The present invention relates to nebulizer apparatus used in respiratory therapy and in particular to continuously connected, continous flow nebulizers used in respiratory therapy.

BACKGROUND AND DESCRIPTION OF RELATED ART

Critically ill patients requiring mechanical ventilation are often victims of respiratory distress syndrome, status asthmaticus and pulmonary infections. Treatment of these and other severe respiratory conditions includes medications delivered directly to the lungs of the patient. Nebulized or aerosolized solutions are the preferred method of delivery of respiratory medication because the medicant is fragemented into small particles that are more efficiently deposited near sites of drug activity in the lung.

Nebulizers are well known in the art. Aerosolization of medications is performed by putting a liquid product in a chamber (nebulizer vial) that has a pressurized flow of gas through it. Utilizing the Bernoulli principle, liquid is drawn through an aspirator tube into the path of a high velocity gas and is fractured into a mist. The mist flows out of the nebulizer by inertial forces.

Current conventional aerosol drug therapy involves administering a finite quantity (dose) of medication deposited into the nebulizer vial and administered until the vial is empty. In normal practice, the period of delivery of each dose is measured in minutes or fractions of an hour. Depending upon the severity of the illness and the duration of activity of the medication, this process is repeated periodically at variable frequencies.

Such intermittent drug administration has the inherent results of (1) subjecting the patient to "peaks" and "valleys" of drug dosage effects, (2) requiring respiratory therapy personnel to periodically service the needs of the patient and nebulizer by measuring doses, disconnecting, filling and reconnecting the nebulizer and periodically monitoring the administration, and (3) disconnecting the patient from an attached ventilator during nebulizer service. Further, medication which is administered as a large volume, such as a surfactant, now requires large medicant flow volume through the nebulizer requiring frequent servicing and refilling of the nebulizer vial which intereferes with ventilator function.

In some cases, a significant porportion of the respiratory flow to the patient is through the nebulizer such as in the operational use of the VISAN nebulizer of Burroughs Wellcome Company. In the delivery of the medicant EXOSURF, up to half of the tidal volume flows through the nebulizing ports of the nebulizer to unite with the balance of the respiratory gas delivered directly from the ventilator in a Y-shaped junction in the flow path to the patient downstream from the nebulizer. In such delivery, the nebulizing gas is synchronized with the nebulizer such that nebulizing gas is delivered to the nebulizer only during the ventilatory inhalation cycle.

A nebulizer comprising a vial-like nebulizing chamber which comprises a two-position flow control valve assembly for accessibly draining and refilling the nebulizing chamber is disclosed in U.S. Pat. No. 4,805,609. While the valve assembly provides access for resupplying a medication dose while the nebulizing chamber remains in sealed relation with the nebulizer, such resupply is service intensive and limited to volumes containable by the nebulizing chamber.

Recent developments in respiration therapy involve aerosolization and delivery of the nebulized mist on a continuous basis over several hours. For example, an entire day's medication dosage is delivered at a constant rate over twenty-four hours, as opposed to conventionally delivering the same dosage for four separate aliquots at six hour intervals. Such delivery eliminates the "peak" and "valley" effects of the drug, reduces respiratory personnel support time, and also reduces the number of times critical medication/nebulizer interconnection is interrupted, thereby diminishing the potentially dangerous exposures of the patient to the effects of respiratory circuit contamination.

Delivery of medicated mist is both in combination with a ventilator and through masks, mouthpieces, and other voluntary mist inhalation apparatus.

BRIEF SUMMARY AND OBJECTS OF THE INVENTION

In brief summary, this invention alleviates all of the known problems related to conventional contemporary administration of nebulized medicants. A nebulizer attachable nebulizer vial, a large supply vessel, and a fluid delivery system are provided for use in combination with a conventional nebulizer. The fluid delivery system provides delivery of aerosolizable fluids continuously from the large supply container into the nebulizer vial without removing the vial from the nebulizer. The nebulizer vial releasably attaches to at least one nebulizer which is available in the art. For critically ill patients, the nebulizer and continuous flow nebulizer vial are used, as part of a nebulizer/ventialtor circuit. For voluntary respiratory patients, the nebulizer and continuous flow nebulizer vial output is directed to a mouthpiece, a mask, or inhaled directly from the nebulizer.

The nebulizer vial comprises at least one inlet port wherethrough influent flow is provided to maintain an adequate reservoir in the vial to support a predetermined effluent flow of fluid to the nebulizer. The influent flow of fluid to the nebulizer via is controlled by a variable such as an IV drip rate control valve. Liquid flow rates and associated nebulization rates are calibrated to match ventilator and desired drug administration rates. Based upon the pressure and flow rates of nebulizing gas a nomogram provides the associated pump rate for influent fluid delivered to the nebulizer vial through the influent port.

In one embodiment, another port drains the nebulizer when the reservoir overfills, thereby providing a fluidic closed loop control of the amount of liquid continuously maintained in the nebulizer vial. As the reservoir provides adequate liquid volume for a longer time than is required to change connections from a drained large supply container in all embodiments of the invention, supply containers are changed without affecting delivery of medication to the patient by closing off nebulizer vial influent and effluent tubes attached to the emptied large supply container, detaching all influent and effluent tubes from the emptied vessel, and attaching the removed influent and effluent tubes to a replacement large supply container, and reopening the tubes.

As it is often desirable to change medication during treatment of a patient, this invention provides apparatus and methods for teminating one medication and initiating another medication without detaching the nebulizer vial. For some medications, it is desirable to synchronize the delivery of the aerosolized mist with a particular portion of a cycle of a ventilator or of a voluntary respiratory cycle. Method and apparatus for changing the synchronization pattern of aerosolized mist delivery in conjunction with the respiratory pattern provides the opportunity to change both medication and the associated medication delivery pattern without disconnecting the nebulizer vial.

From time-to-time, as appropriate, it may be necessary to add a special medication to the reservoir in the nebulizer vial or to draw fluid from the nebulizer vial. An attachable add-site device is provided which is penetrable by a syringe needle but which maintains a seal during needle penetration and after removal of the needle, thereby providing access to the inside of the nebulizer vial for non-vial-detaching intervention.

As a guard against problems of over and under filling the reservoir in the nebulizer vial, a closed loop control circuit is provided. The control circuit comprises liquid level sensors and pump controls and alarms to protect the safety of the patient.

To improve efficiency of medicant nebulization, temperature of fluid delivered to the nebulizer vial is varied to conform with optimum nebulization temperatures of a particular mediant. Also, to achieve optimum uptake and patient response to a medicant, temperature of inspirational fluid is adjustably controlled.

Accordingly, it is a primary object to provide apparatus and methods whereby a continuous supply of aerosolized medication is provided to a patient through a nebulizer.

It is another primary object to supply the aerosolized medication over a period of time measured in tens of hours or days substantialy without manual intervention once delivery of medication has begun.

It is another primary object to provide a source of medication or other fluid from a large supply vessel on a continuous basis such that the inherent fluid capacity available for storing fluid in a nebulizer vial does not restrict the amount of time medication is continuously delivered or the amount of medication which can be delivered to a patient before the nebulizer via is separated from the nebulizer.

It is another primary object to provide a nebulizer vial comprising at least one port through which a fluid reservoir inside the vial is continuously replenished, the nebulizer vial being attachable to at least one nebulizer which is available in the art.

It is another object to provide a flow controller for influent fluid delivered to the nebulizer vial from a large supply container to the nebulizer vial fluid replenishment port such that the rate of replenishment of fluid in the nebulizer vial is substantially the same as the rate of fluid lost through nebulization.

It is another object to provide at least a second port to the nebulizer vial whereby excess fluid in the reservoir inside the nebulizer vial is drained.

It is another object to provide a closed loop control system comprising a pump, the nebulizer vial, and the large supply vessel whereby a substantially constant volume reservoir is maintained in the nebulizer vial as long as fluid remains in the large supply vessel.

It is another object to provide a method for replacing a used large supply vessel with another large supply vessel without affecting the administration of nebulized fluids to the patient.

It is an important object to provide a method and apparatus for changing delivery of medicants to the nebulizer vial form one medicant to another without detaching the nebulizer vial from the nebulizer.

It is an important object to provide a method and apparatus for changing delivery of medicant to the nebulizer vial from one medicant to another by throwing an electrical switch.

It is an important object to provide a method and apparatus for changing delivery of medicant to the nebulizer vial from one medicant to another by selecting flow from a different large supply vessel by via a manually operated, multiple position fluid valve.

It is another important object to provide an add-site wherethrough fluid is delivered to or withdrawn form the nebulizer vial without detaching a connecting line between the influent fluid source and the nebulizer vial.

It is an object to provide methods and apparatus to selectively control synchronization of operation of the nebulizer with the portions of cycles of an attached ventilator.

It is a basic object to provide a liquid level controller of the liquid level in the nebulizer vial reservoir whereby delivery of influent fluid to the nebulizer vial is terminated if the reservoir overfills and an alarm is sounded if the reservoir is overly depleted.

It is another basic object to provide a method and apparatus for adjustably controlling the temperature of influent fluid to the nebulizer prior to delivery to the nebulizer and nebulization.

It is another basic object to provide a method and apparatus for adjustably controlling the temperature of nebulized fluid and other inspired gases delivered to the patient.

These and other objects and features of the present invention will be apparent from the detailed description taken with references to accompanying drawings.

BRIEF DESCRIPTION OF THE DRAWINGS

FIG. 4 is a segmented perspective of an inverted medication bag representing the large supply vessel and a effluent lead compressed to prevent fluid from draining from upstream connections and removed from the large supply vessel.

FIG. 5 is a segmented perspective of a continuous flow nebulizer system comprising a mouthpiece interface to a patient for voluntary respiratory therapy.

FIG. 6 is a segmented perspective of a nebulizer/nebulizer via medicant delivery system comprising a nebulizing gas flow input through the bottom of a nebulizer vial and a top medication input through a nebulizer connected effluent tube partially cut away to show delivery of medicant, the effluent tube delivering aerosolized mist to a patient through mask.

FIG. 10 is a table of time-varying waveforms representative of ventilator operation and selectable options for respiratory rate, synchronized operation of the nebulizing gas control system as controlled by a mode selectable controller.

FIG. 11 is a segmented perspective of a nebulizer vial and an add-site device where fluids are added to or removed from the nebulizer vial without separating the vial from either the nebulizer or influent fluid supply lines.

FIG. 12 is a partially exploded perspective wherein the attachable nebulizing vial is seen apart from the nebulizer, the nebulizing vial comprises a plurality of ports whereby fluid is received from a pump and large supply vessel to replenish a reservoir in the vial and overflow fluid is returned to the large supply vessel to limit the level of filling of the reservoir.

FIG. 14 is a perspective of a nebulizer vial seen apart form the nebulizer; the nebulizer vial comprises slots wherein liquid level sensing fingers, seen exploded from the vial, are disposed to sense critical fluid levels; a liquid level controller and a controlled pump are also seen.

FIG. 17 is a circuit schematic for a differential liquid level detector.

FIG. 18 is a logic diagram showing pump control and alarm setting logic for overfill and underfill conditions of the nebulizer vial, respectively.

FIG. 20 is a segmented block diagram of a patient ventilating system which uses the apparatus of FIG. 19 comprising a fluidic control valve attached to a nebulizer which controls intermittent nebulized fluid flow.

FIG. 22 is a perspective of the nebulizeable fluid cooling container seen in FIG. 20 with parts removed for clarity of presentation.

DETAILED DESCRIPTION OF THE ILLUSTRATED EMBODIMENTS

In this description, the term proximal is used to indicate the segment of the device normally closest to the patent when it is being used. The term distal refers to the other end. Herein the term nebulizing device is defined to be a nebulizing unit or instrument used to aerosolize fluid for delivery to a patient. The term nebulizer vial is defined to be that portion of a nebulizing device which comprises a container for a reservoir for fluid to be nebulized. The term nebulizer is defined to be the non-nebulizer-vial portion of the nebulizing device which comprises at least a portion of the nebulizing mechanism. Reference is now made to the embodiments illustrated in FIGS. 1–22 wherein like numerals are used to designate like parts throughout.

Figure 1:
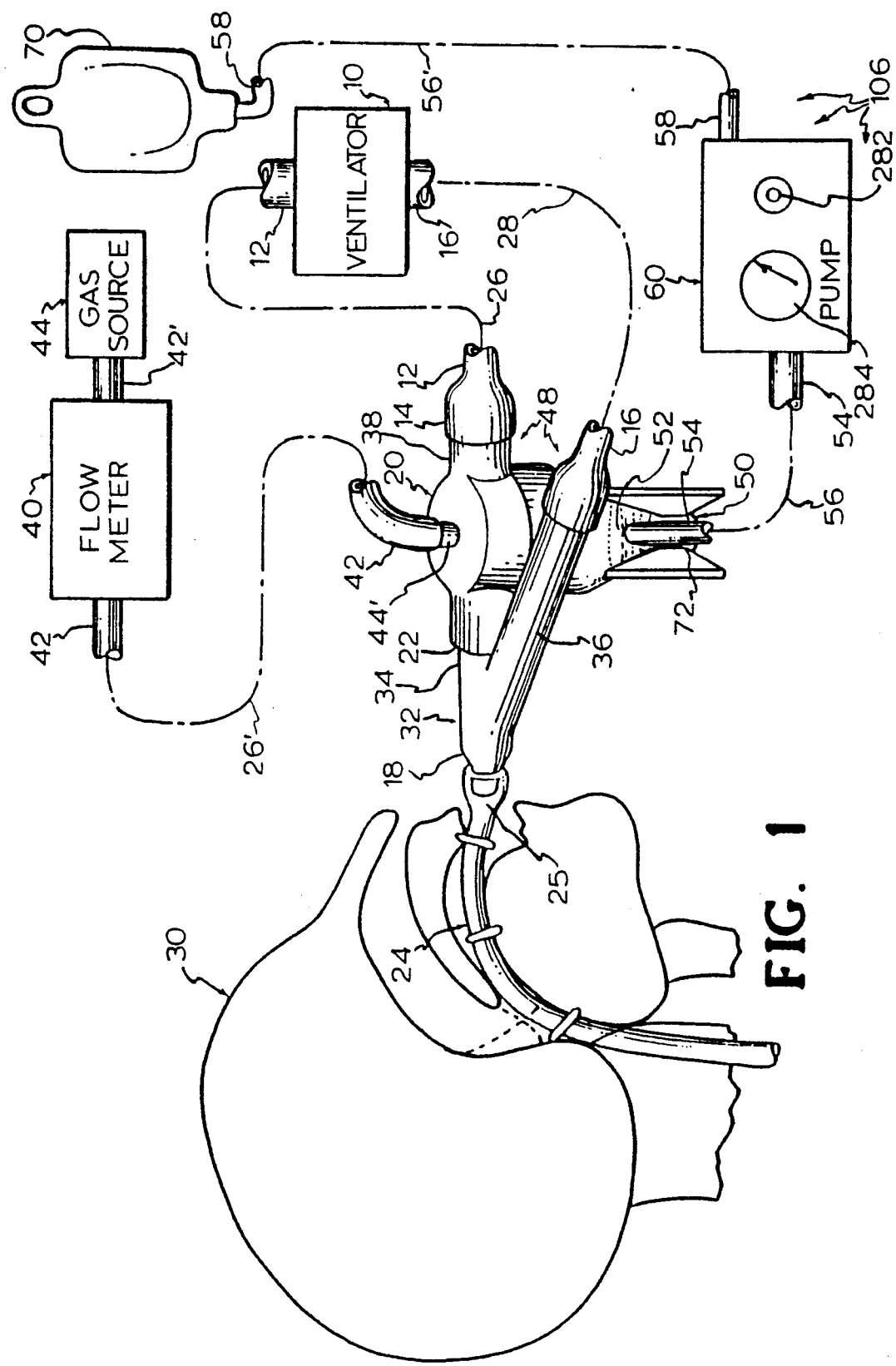
FIG. 1 is a schematic representation of a patient receiving respiratory support and continuous medication via a continuous flow nebulizing device interposed between a endotracheal tube and a ventilator.

As seen in FIG. 1, a patient 30, undergoing respiratory therapy, is fitted with an endotracheal tube 24. The proximal trunk end 18 of a "Y"-shaped connector 32 is insertably connected to a distal end 25 of endotracheal tube 24. One bifurcated distal end 34 of "Y"-shaped connector 32, is insertably connected to a proximal port 22 of a nebulizer 20 which is part of a nebulizing device 48. Nebulizer 20 is disposed between distal end 34 of "Y"-shaped connector 32 and a proximal end 14 of a respiratory gas delivery tube 12. Thereat a distal part 38 of nebulizer 20 is insertably connected to gas delivery tube 12. Gas delivery tube 12 provides the distal portion of inhalation respiratory pathway 26 and connects to the output inhalation gas of a ventilator 10. Ventilator 10 therapy supplies periodic, breath sustaining pulses of pressurized gas through tube 12, nebulizer device 48, and "Y"-shaped connector 32 into endotracheal tube 24 and to patient 30.

The other distal end 36 of "Y"-shaped connector 32 comprises a proximal portion of an exhalation respiratory pathway 28 which further comprises tube 16 which returns exhalation flow to ventilator 10. Many different ventilators are known and available in the art. Generally, ventilators which are currently used with nebulizers may be used with the invention.

Nebulizer 20 receives a supply of nebulizing gas from a flow meter 40 along a fluid pathway 26' which passes through a tube 42 interposed and connected between flow meter 40 and a top nebulizer inflow connecting tube 44'. Flow meter 40 receives a pressurized gas from a gas source 44 through a connecting tube 42'. Gas pressure from gas source 44 is sufficient to provide the volumetric flow for which flow meter 40 is preset. Gas source 44 may comprise pressurized oxygen or other breathable gas from the hospital pressurized $O_2$ delivery system, from a tank of compressed oxygen, a blender, directly from ventilator 10 or from other sources of pressurized gases used in respiratory therapy. Flow meters are well known and widely used in the art. Such flow meters may comprise macro and vernier adjustable controls for very accurate and precise gas flow settings. Although $O_2$ is preferred for some selected medicants, source 44 may supply oxygen blended with other gases.

Nebulizing device 48 comprises nebulizer 20 which operates in combination with an attached nebulizer vial 50. Nebulizing device 48 nebulizes or aerosolizes fluids contained as a reservoir 72 in nebulizer vial 50 thereby producing a mist which is carried to patient 30 by influent flow of gas from ventilator 10 through pathway 26 and by nebulizing gas received from gas source 44. Delivery of nebulized fluid to patient 30 is therefor dependent upon the availability of fluid resident in the reservoir 72 at any given moment.

Figure 2:
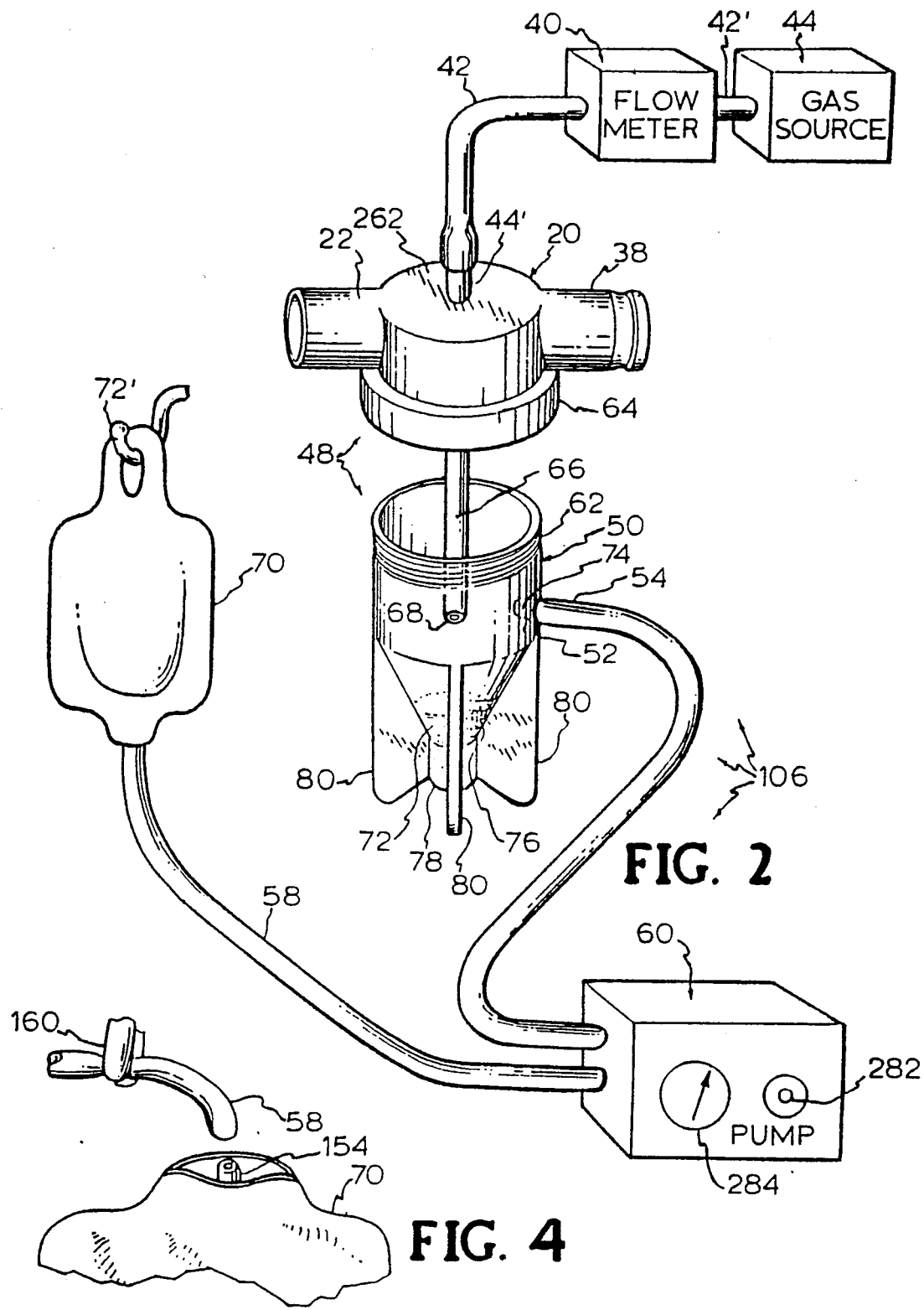
FIG. 2 is an exploded perspective of a nebulizer and a continuous flow supporting system comprising a large medication storage vessel, a rate controllable pump, an influent port accessible nebulizer vial separated from the nebulizer, and influent fluid flow regulating and supply devices.

In the currently preferred embodiment seen in FIGS. 1 and 2, a continuous flow system 106 provides substantially continuous delivery of fluid of nebulizer vial 50 to maintain the volume of liquid at an adequate and essentially unchanging level in reservoir 72. Continuous flow system 106 comprises nebulizer vial 50, at least one influent access port 52 to nebulizer vial 50, connecting at influent access port 52 to nebulizer vial 50, connecting tubing 54 interposed between a pump 60 and connected at influent access port 52, the pump 60, additional tubing 58 providing medicant pathway 56' interposed between and connected to pump 60 and a large medicant supply vessel 70, and the large medicant supply vessel 70. As continuous flow system 106 maintains a constant volume of liquid in nebulizer vial 50, continuation of delivery of aerosolized fluid is not solely dependent upon the initial contents of reservoir 72 at the time nebulizer vial 50 is joined to nebulizer 20, but upon the larger volume available in large medicament supply vessel 70. Such supply vessels may be IV gas, bottles or other nebulizing medication and reagent containing vessels from which therapeutic liquids are drawn.

As seen in FIG. 2, nebulizing device 48 comprises nebulizer vial 50 which releasably and sealably attaches to nebulizer 20. Such attachment may be by a male threaded member 62 of nebulizer vial 50 insertably joined to a female threaded member 64 of nebulizer 20. When nebulizer 20 is so disposed and is connected to nebulizer vial 50, an end 68 of an aspirator tube 66 is disposed below the surface of a reservoir 72 in the bottom of nebulizer vial 50 as best seen in FIG. 3.

Nebulizer 20 may be a commercially available nebulizer device generally used for administration of aerosolized fluids and is therefore used as purchased. Nebulizer vial 50, on the other hand, comprises a container made to releasably but sealably attach to commercially available nebulizer 20 and, in combination with a gravitational or mechanical pump and a large supply vessel, provide a continuously filled reservoir 72 from which medicants are aspirated via aspirator tube 66 into nebulizer 20 and aerosolized.

Figure 3:
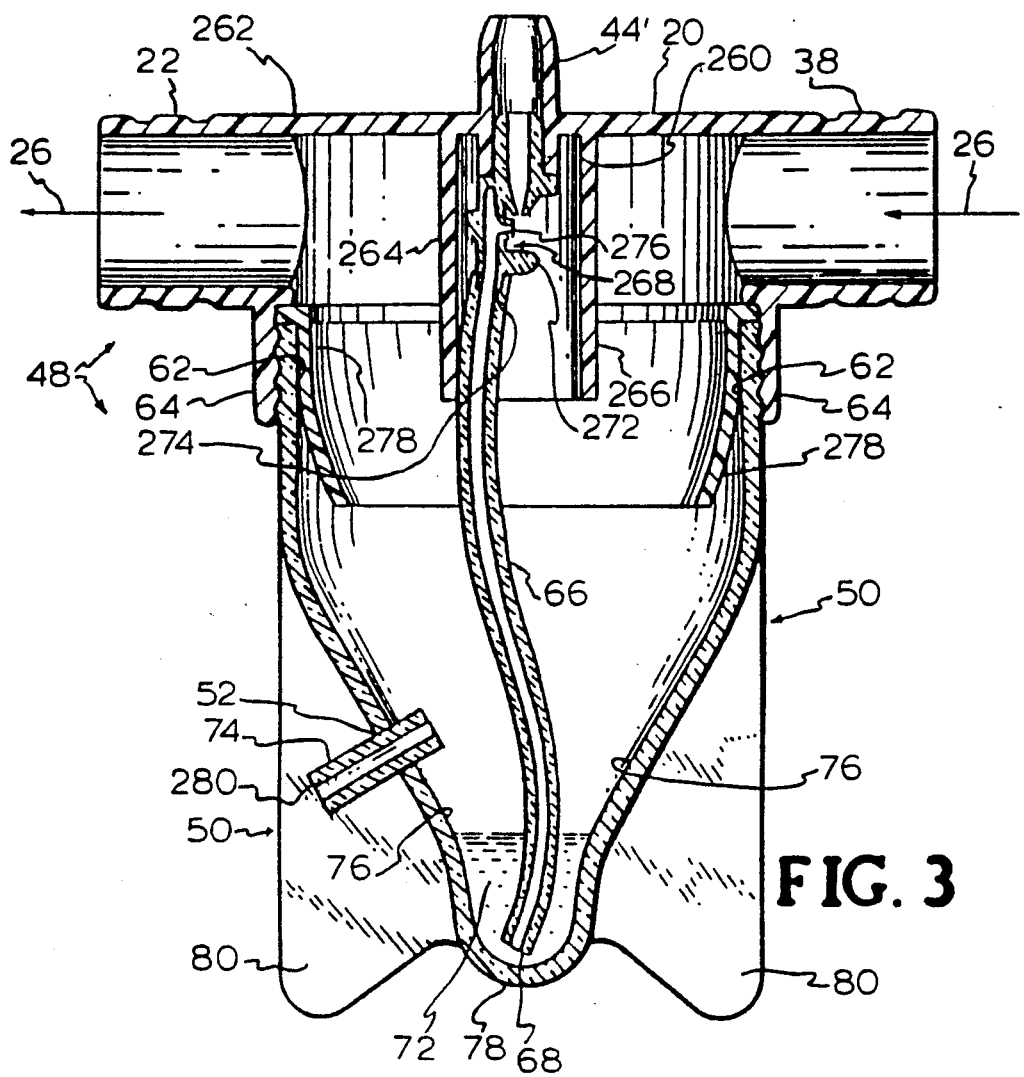
FIG. 3 is a cross section of the nebulizer of FIG. 2 joined to a nebulizer vial comprising an influent port.

FIG. 3 provides a sectional view of nebulizing device 48, comprising nebulizer 20 theadably interconnected to nebulizer vial 50. The following description of nebulizer 20 is provided for a general understanding of the interaction between nebulizer 20 and nebulizer vial 50.

Nebulizer 20, as seen in FIG. 3, comprises a housing 262 which comprises a top nebulizer inflow connecting tube 44', a nozzle 260, a baffle assembly 268, and aspirator tube 66. Baffle assembly 268 further comprises an aspirator tube connecting orifice 274, a liquid effluent orifice 276, and a baffle plate 272. Pressurized gas which provides the nebulizing high velocity stream for nebulization is provided through top nebulizer inflow connecting tube 44'. The high velocity stream is produced by nozzle 260 in the direction of baffle plate 272. As the high velocity stream passes by liquid effluent orifice 276 a resulting below ambient pressure between orifice 276 and end 68 of aspirator tube 66 which is sufficient to draw liquid from reservoir 72 to orifice 276 and further draw a small amount of liquid through orifice 276 which is carried by the high velocity stream to impact against baffle plate 272 to thereby produce a mist.

Housing 262 further comprises a pair of baffles 264 and 266 which lie in inhalation pathway 26 and shield the space where nebulization occurs. A hollow frusto-conical baffle 278 is disposed in the medial space between inhalation pathway 26 and the extension of baffles 264 and 266 to limit air flow into nebulizer vial 50 and aid in entraining mist into inhalation pathway 26. While this description of the nebulizer is for a single connecting tube 44', nozzle 260 and associated parts, the number of inflow connecting tubes, nozzles, and associated nebulizer parts may vary in selected commercial nebulizers as is well known in the art.

Nebulizer vial 50 has essentially the same inverted, general cap-like shape of available single-dose nebulizer vials, is made from synthetic resinous materials and is preferably transparent for easy monitoring by a respiratory technician or other patient attendant. The materials of construction of nebulizer vials are well known in the art. They are usually of chemically-inert thermoplastic such as polyolefins or polyvinyl chlorides. Their selection and fabrication are well within the skill of the art.

As seen in FIGS. 2 and 3, nebulizer vial 50 comprises a port 52 and a therethrough inserted feedthrough 74. Also as seen in combination in FIGS. 2 and 3, port 52 may be located at different sites in nebulizer vial 50 as required to meet tubing placement and other physical fluid delivery restrictions. As seen in FIG. 2, tube 54 is engaged about feedthrough 74 to be releasably but snugly affixed thereat in pressure-sealed relation. Feedthrough 74 comprises a through hole 280, as seen in FIG. 3, through which fluid received under pressure from pump 60 flows into nebulizer vial 50. The bottom of the nebulizer vial 50 comprises an inverted conically shaped part 76. Apex 78 of inverted conically shaped part 76 provides a low point for fluid contained in reservoir 72 where aspirating tube 66 end 68 is normally disposed when nebulizer 20 is affixed to nebulizer vial 50. A plurality of legs 80 provide a level support when nebulizer vial 50 is disposed on a horizontal surface to maintain fluid at the bottom of inverted conically shaped part 76.

Referring again to FIG. 2, large supply vessel 70, seen to be in the form of a plastic container bag, is disposed on a hook 72', such as an IV bag is hung on in general medical practice. Tube 58 provides the fluid pathway to pump 60. Pump 60 comprises rate control dial 282 and flow rate display 284 which provide for manual flow rate adjustment. Thereby, the flow rate of pump 60 is set to provide a rate of flow of liquid into nebulizer vial 50 which is substantially equal to the rate of loss of liquid from the reservoir 72 through aerosolization. Such a flow rate for pump 60 is derived from a nomogram which comprises the variables of gas flow through flow meter 40 and through ventilator 10. A different nomogram is generated for each combination of nebulizer 20, flow meter 40, and ventilator 10. Derivation of such nomograms is well within the skill of the art. As disclosed above, pump 60 is a variable flow controlling pump which provides and maintains an accurate and precise flow rate. Pump 60 may be a syringe infusion pump, model number 2001, available from Medfusion, a Medox, Inc. Company, 3450 River Green Court, Duluth, Ga. 30136.

Another currently preferred embodiment of the invention comprises a nebulizing device 48' as seen in FIG. 5. Nebulizing device 48' further comprises a nebulizer 20' and a nebulizing vial 50'. Nebulizer 20' is a commercially available nebulizer comprising a superiorly disposed "T" connection 292 which provides a junction wherein aerosolized mist merges in inhalation pathway 294 with inhaled gas for transport to the lungs of patient 30.

In this example, patient 30 is breathing by voluntary respiration and no ventilator is involved. However, a ventilator can be used with this currently preferred embodiment in the same manner ventilator 10 was employed in the embodiment disclosed hereinbefore. The patient 30 interface is a mouthpiece 286 which interconnects to proximal end 34' of proximal port 22' of "T" connection 292. Such mouthpieces are known and available in the art. As no ventilator is used, inhaled and exhaled gases enter and exit, respectively, a single distal port 288 of "T" connection 292.

In this non-ventilator application, nebulizing gas is provided from a gas blender 292 through flow regulator 40. Such gas blenders mix gas to a predetermined blend from breathable gas sources seen to comprise a primary gas source 360 and secondary gas source 362, as seen in FIG. 5. In general, gas sources for gas blender 292 may be greater in number than the exemplary primary source 360 and secondary source 362. Also such sources may comprise a mix of gases such as compressed air, $O_2$ from a tank or hospital line, a tank of pressurized gas, or directly from the ventilator. In every case, gas blender 292 receives flow through input tubes, such as tubes 364 and 366, and accurately meters a mix of the gases to thereby supply a blend to flow meter 40. Gas blender 292 and flow meter 40 may be the same device. Gas blenders are well known and widely used in the art. Nebulizing gas is delivered in a standard manner into nebulizer 20' via gas feedthrough 44" disposed in a planar top surface 296 of nebulizer 20'.

Fluid to be aerosolized is provided by a gravity feed from large supply vessel 70 superiorly disposed from a hook 72' in the same manner as an IV bag is disposed for intravenous fluid injection to a patient. A drip rate controller 82, similar to an IV drip rate controller, is interposed in the nebulizing fluid pathway between large supply vessel 70 and nebulizing device 48'.

The "T" connection 292 of nebulizer 20' is modified to comprise a nebulizing fluid entry tube 74' which extends from a superior position at the top of "T" connection medially through the stem 298 of "T" connection 292 to an inferior end 300 disposed inside nebulizer vial 50'. A drop 302 of influent fluid is seen appearing at end 300 of tube 74' in FIG. 5. Thus, in this embodiment, nebulizer 20' is modified to comprise nebulizing fluid entry tube 74' to provide constant, continuous delivery of nebulizing fluid from a large supply vessel 70 into unmodified nebulizing vial 50' through a top entry tube 74'.

Nebulizing fluid is supplied to maintain a constant fluid volume in nebulizer vial 50' by a predetermined adjustment of drip rate controller 82. Aspirator tube 66 aspirates liquid from reservoir 72 into an aerosolizing nozzle (not shown) of aspirator 20'. Medicant or other nebulized reagent is delivered from large supply vessel 70 disposed from a hook 72' superiorly positioned above patient 30 as an IV is positioned to provide a positive head of pressure at drip rate controller 82. Nebulizing fluid is thereby continuously provided to reservoir 72 and therefrom aerosolized for delivery to patient 30.

In another currently preferred embodiment seen in FIG. 6, standard nebulizing device 48" comprises a commercially available nebulizer 20" and nebulizer vial 50" and a vertical top entry tube 304. In this embodiment, nebulizer 20" and 50" are unmodified before use. As is standard for nebulizing device 48", an entry port 306 for upward streaming nebulizing gas is disposed in the bottom of nebulizer vial 50". An influent feedthrough 308 comprises the nebulizing gas entry pathway for nebulizing device 48". Influent feedthrough 308 comprises an inferior end 314 which comprises tube 42 attachment outside nebulizing device 48". Thereat a tube 42 delivers nebulizing gas into a medial orifice 368 in feedthrough 308 from a flow meter 40 and gas source 44 in the same manner as previously disclosed.

Superior end 316 of feedthrough 308 comprises a butt end. A hat-shaped part 310 comprises a brim 312 and a crown 318 which is disposed over superior end 316. The inner diameter of crown 318 is larger than the exterior diameter of feedthrough 308 thereby providing a capillary pathway for fluid flow to rise therebetween. Further, hat-shaped part 310 comprises a nozzle sized orifice 320 in the top center of crown 318 juxtaposed the medial orifice 368 of feedthrough 308. Thus, when gas is delivered into nebulizer device 48" from flow meter 40 and gas source 44, fluid residing in the inside bottom of nebulizer vial 50" is drawn across the bottom of brim 312 and into the capillary space between crown 318 and feedthrough 308 and therefrom into the stream exiting medial orifice 368 of feedthrough 308 to pass through nozzle sized orifice 320.

The stream exiting nozzle sized orifice 320 impacts a baffle plate 274' thereby shattering the captured fluid into a fine aerosolized mist. The mist rises with discharging gas through the only effluent tube 322 in nebulizing device 48". Releasably affixed about effluent tube 322 is a vertical top entry tube 304. Vertical top entry tube 304 comprises a large effluent port 324 wherefrom the fine aerosolized mist passes for inhalation by a patient.

Vertical top entry tube further comprises a feedthrough 74" through which a nebulizing fluid, delivered from a large supply vessel, is flow rate controlled by a drip rate controller, in the same manner as earlier described. Parts of top entry tube 304 are cut away to reveal a drop 302' of liquid entering top entry tube 304 from feedthrough 74". Each drop 302 proceeds downward until disposed at the level of hat-shaped part 310 where it merges with liquid forming the reservoir in nebulizer vial 50" to be drawn therefrom by capillary action to be aerosolized.

To use nebulizing device 48", a patient may inhale the mist exiting from large effluent port 324 directly or place a "T" connector similar in size and shape to "T" connector 292 seen in FIG. 5 for use with a mouthpiece 286 as also seen in FIG. 5 or a ventilator as seen in FIG. 1. However, patient 30 is seen breathing mist via a mask 370 directly, but releasibly, affixed to top entry tube 304. Mask 370 comprises a mist receiving inlet tube 372, a facial structure adapting in closure 374 at least one orifice 376 providing a passage for access to room air, a nose band 378, and an adjustable head band 380. To use mask 370 in combination with nebulizing device 48", inlet tube 372 is insertably joined to top entry tube 304 at part 324 such that nebulized mist exiting nebulizing device 48" passes through inlet tube 372 into enclosure 374.

Mask 370 is firmly affixed to patient 30 by placing enclosure 374 over the nose and mouth of patient 30. Head band 380 is place around the head of patient 30 and tightly drawn to maintain enclosure 374 over the nose and mouth of the patient without any other support, thereby suspending nebulizing device 48" from mask 370. Nose band 378 is pinched to comfortably contact the upper portion of enclosure 374 with the nose of the patient for additional support and a better match of the mask enclosure to the facial structure of patient 30.

So disposed, nebulizing device 48" continuously delivers medicant mist to voluntarily respirating patient 30. A resupply of nebulizing fluid is supplied through feedthrough 74". Fluids flow downward from feedthrough 74" through the upward path of medicated mist to the vicinity of hat shaped part 310 to form the reservoir from which fluids are drawn and aerosolized to form the mist.

Another currently preferred embodiment is seen in FIG. 7. As a patient may require a plurality of different medications during a continuous period of respiratory therapy, this embodiment provides for selectable delivery of medication from any one of large supply vessels 70, 70', or 70" as selected at a pump selection and control box 90 or by solely turning on a single selected pump manually. Although three supply vessels 70, 70', and 70" are seen in FIG. 5, the number of vessels and pumps is increased or decreased, as needed for patient therapy, and is not restricted to three.

Each large supply vessel 70, 70', and 70" is connected by a tube to an identical pump 60. Each pump 60 is therefrom connected to a plenum 92 by short tube 88, 88', and 88" associated with each large supply vessel 70, 70', and 70" respectively. Each short tube 88, 88', and 88" conects to a connecting leg 326, 326', and 326", respectively, which comprises a small diameter channel and connects thereby to plenum 92. Plenum 92 comprises a connecting and delivering channel (not shown) of small diameter such that essentially no mixing takes place at the intersection of the small orifices of legs 326, 326', and 326". A pathway from the connecting and delivering channel of plenum 92 to the inside of nebulizer vial 50 is provided by attachment to feedthrough 74.

Each pump 60 is exclusively turned on or off by a pump selection and control device 90. Pump selection and control device 90 comprises an ON/OFF switch 94 which controls power to the pumps. Further, pump selection and control device 90 comprises a pump selection switch 96 whereby power is exclusively applied to one pump 60 at a time. An electrical connection is made to each individual pump 60 through electrical cables 120, 120', and 120", each cable being associated with a particular pump 60 and thereby associated with large storage vessels 70, 70', and 70", respectively. Alternatively, an individual pump 60 is exclusively selected by switching an individual pump 60 "ON" to provide selected medicant delivery to nebulizer vial 50 using the control dials and switches available on each individual pump 60.

When a pump 60 is selected, that pump 60 responds by pumping fluid from its associated large storage vessel 70, 70', or 70" to supply fluid through associated short tube 88, 88', or 88" internally through plenum 92 and into nebulizer vial 50 via selected tube 88, 88', or 88" and feedthrough 74. Any residual medicant, as provided by the last used pump 60 and resident in plenum 92 and feedthrough 74 is pumped into nebulizer vial 50 ahead of the newly selected medicant. Care must be taken that such medicants can be safely mixed.

As mentioned above, the flow rate of each pump 60 can be set individually. However, when pump selection and control device 9 is used, a single dial 98 is used to set a common flow rate for all of the pumps. Electrical switches, circuits, and components used in selection and control device 90,are known and available in the art.

In addition to changing the medicant delivered to a patient 30 while nebulizer 20 and nebulizer vial 50 are continuously attached, it is sometimes desirable to change the mode of delivery of medicant. As an example, one medicant is prescribed to be aerosolized and delivered continuously. Another medicant is prescribed to be aerosolized only during patient 30 inspiration. Yet another medicant is prescribed to be aerosolized during exhalation of the patient to build a bolus which enters into the lungs of patient 30 only on the leading edge of inspiratory flow. Still another medicant is prescribed to be delivered during a portion of each exhalation and inhalation cycle. As seen in FIG. 8, a mode control valve 100, which is activated by signals from a valve controller 100' which responds to signals from ventilator 10 to respondingly turn pressure to the nebulizer "ON" and "OFF" as a function of a selected delivery control option to control the frequency and timing of nebulization relative to operation of ventilator 10.

Referring to FIG. 10, four control options are seen. The ventilator cycles are referenced to inhalation cycle segment 340 and to exhalation cycle segment 342. "ON" segment 340 defines the period of inhalation. Similarly, "OFF" segment 342 represents exhalation. Option 1 comprises a continuously "ON" waveform 344 whereby the ventilator cycles have substantially no effect upon nebulization. Option 2 comprises a mode wherein mode control valve 100 is open producing an "ON" waveform 344 when ventilator inhalation cycle segment 340 is present and an "OFF" waveform 346 when segment 342 is present. Option 3 comprises a mode wherein mode control valve 100 is closed in synchronism with segment 342 and is open in synchronism with segment 340. Option 4 comprises a mode wherein mode control valve 100 is opened a predetermined period after ventilator 10 turns "ON" and is closed another predetermined period after ventilator 10 turns "OFF". Option 4 is so timed to reduce clogging of filters in the ventilator system.

A block diagram of a fluidic control for a valve 100 is seen in FIG. 9. Rather than controls derived electrically from ventilator 10, as seen in FIG. 8, a flow sensor 104 is placed in the pathway 26. A flow sensor amplifier and control device 106 is connected to flow sensor 104 through electrical cable 104' and provides the same mode controls to valve 100 as ventilator 10 provides in the circuit of FIG. 8. Such flow sensors and circuits for controlling valves are well known and widely used in the art.

From time-to-time, it is desirable to add medicants or other fluids directly to reservoir 72 of nebulizer vial 50 or to withdraw fluids therefrom. An add-site device 112 is seen in FIG. 11 whereby a syringe needle 108 is inserted through a pierceable membrane shroud 328 for access to fluids in direct communication with the reservoir of nebulizer vial 50. Add-site device 112 comprises a "Y" shaped body 118 which firmly and sealingly is affixed to nebulizer vial 50 in place of feedthrough 74, a side-leg 114 which comprises a connection to tube 54 from pump 60 for receipt of influent medicants as described above and another side-leg 116 which is affixed on an open end 336 to a cap 122. Cap 122 comprises a cylindrical side wall 332 and an orifice 334 disposed in the top. Snugly interposed between cap 122 and open end 336 is a pierceable shroud 328 which also covers open end 336. Orifice 334 provides access to shroud 328, thereat. Shroud 328 comprises flexible, elastic synthetic resinous material which reluctantly parts as syringe needle 108 is piercingly inserted therethrough, providing access into the orifice of side-leg 116. However, shroud 348 comprises sufficient elasticity to close snugly over the barrel inserted of needle 108. While syringe needle 108 is inserted contents of associated syringe 110 are deposited into add-site device 112 or, conversely, contents of add-site device 112 and therefore contents of the reservoir of nebulizer vial 50 are withdrawn into syringe 110. Once the activity involving inserted syringe 110 is complete, syringe needle 108 is withdrawn from add-site device 112 and therefore from shroud 334 which elastically closes the access hole of syring needle 108.

Figure 13:
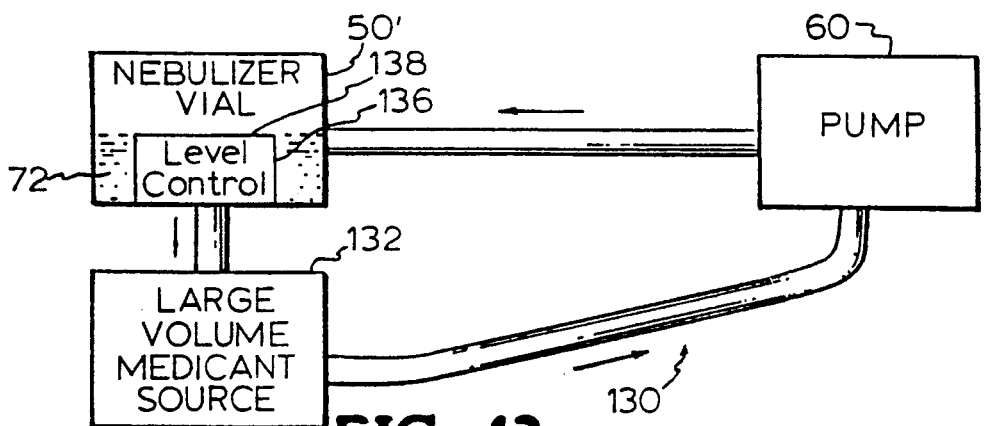
FIG. 13 is a block diagram of the fluid flow control and feedback circuit seen in FIG. 12.
Figure 7:
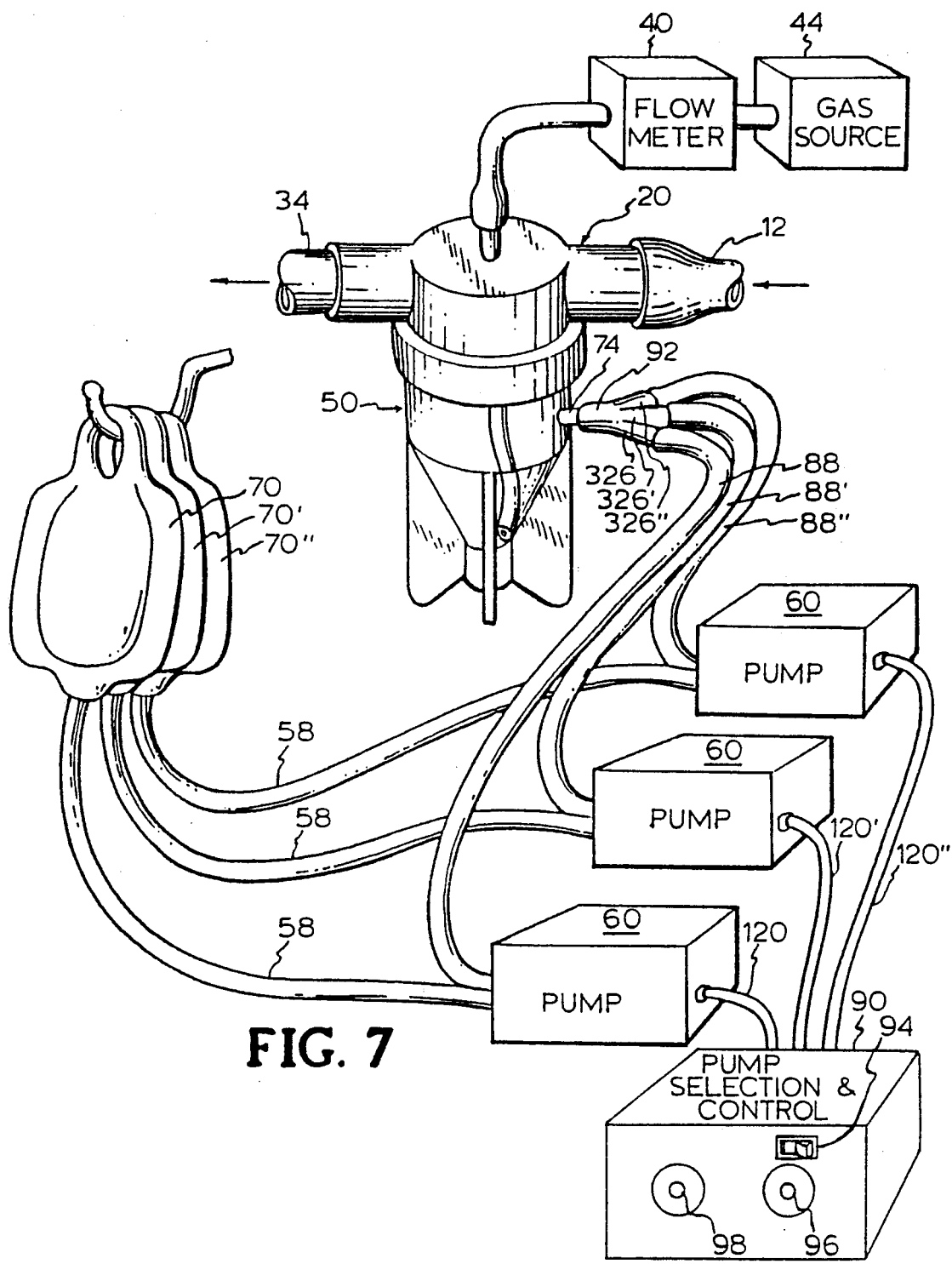
FIG. 7 is a perspective of the nebulizer and continuous flow support system for selectable delivery of one of a plurality of medicants to the nebulizer vial.
Figure 8:
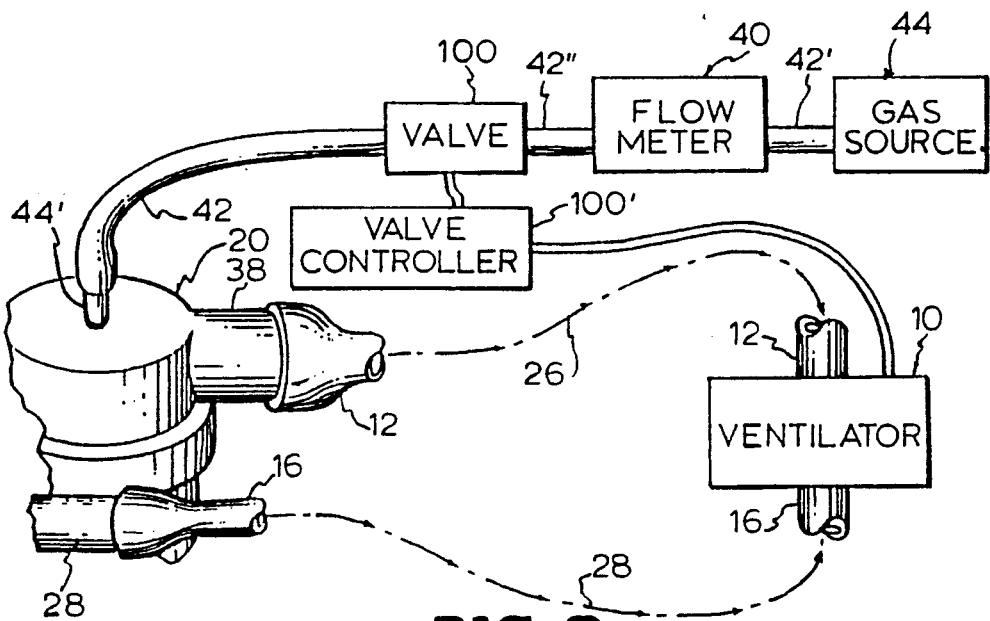
FIG. 8 is a perspective of a segmented portion of the nebulizer, similar to that seen in FIG. 7, wherein a ventilator is interconnected to a valve to thereby control and synchronize the rate of delivery of nebulizing gas to a portion of a respiratory cycle.
Figure 9:
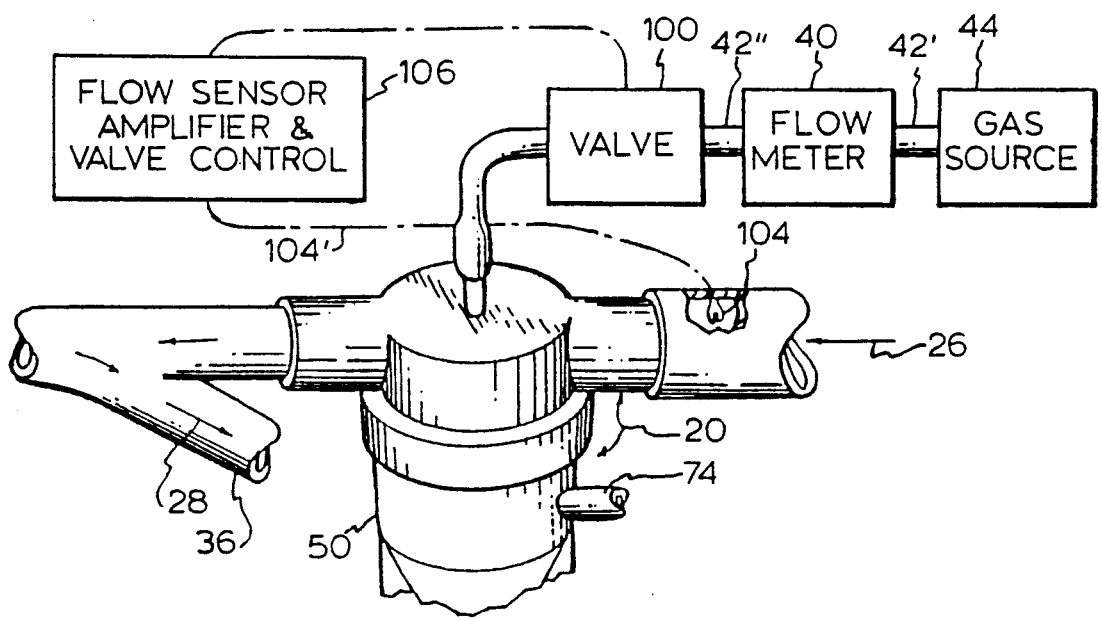
FIG. 9 is a schematic block diagrams of a nebulizing gas control system comprising a flow sensor, in the inhalation pathway of the patient, which provides feedback to a valve controller such that the rate of delivery of nebulized mist is synchronized with a portion of a respiratory cycle.

If influent flow from pump 60 is not precisely set to equal the effluent flow due to nebulization by nebulizer 20, the volume of fluid in reservoir 72 will steadily increase or decrease. A fluidic control system 130, comprising another currently preferred embodiment, which corrects for higher influent flow than effluent flow is seen in FIGS. 12 and 13. As seen in FIG. 12, fluidic control system 130 comprises large supply vessel 132, pump 60, nebulizer vial 50' and interconnecting tubes 54, 58, and 134. Nebulizer vial 50' comprises two feedthroughs, an influent feedthrough 74' which is similar in shape and function to feedthrough 74 seen in FIG. 2 and an effluent feedthrough 136. Each feedthrough 74 and 136 comprises a sturdy tube which is firmly affixed in air and liquid tight relation to nebulizer vial 50' at each site 144 and 146, respectively. Affixing of feedthroughs 74' and 136 to nebulizer vial 50' is accomplished by bonding or welding or by molding the tubes in place as nebulizer vial 50' is molded. All such processes are widely known and used in the art.

Effluent feedthrough 136 comprises an upper end 138 disposed inside nebulizer vial 50' and a lower end 140 disposed for an external connection to tube 134 outside nebulizer vial 50'. Upper end 138 is disposed at the maximum fluid level 142 which reservoir 72 is permitted to attain by the fluidic circuit.

Large storage vessel 132 comprises a straw 148 which communicates to the bottom of the vessel 132 and through an orifice at site 152 in cap 150, with connecting tube 58. A short drain tube 156 is connected to a return port 158 and communicates through the top of cap 150 with connecting tube 134. Fluidic circuit 130 is constructed by attaching tube 58 on one end to straw 148 at site 152 and to pump 60 on the other end. Tube 54 is connected to pump 60 on one end and to feedthrough 74' on the other end. Tube 134 is connected to feedthrough 136 on one end and connecting tube 156 on the other end.

As seen in the block diagram of FIG. 13, fluidic circuit 130 operates to maintain reservoir 72 at a constant level by setting pump 60 to supply fluid at a rate higher than the effluent rate of aerosolization by nebulizer 20 (not shown in FIG. 13). As reservoir 72 is filled to the level of end 138 fluid spills into effluent feedthrough 136 and is returned to vessel 132 (as indicated by a drop 348 forming at the outlet of tube 156 in FIG. 12). Thus reservoir 72 is constantly filled from the significantly larger reservoir contained in large supply vessel 132 allowing continuous nebulizing therapy over a period of hours or days.

Over a long period of continuous nebulization therapy, fluid in the large vessel 70 may also be depleted. In that case, reservoir 72 provides a buffer, permitting a reasonable time for depleted vessel 70 to be replaced. As seen in FIG. 4, replacement is performed by temporarily terminating flow through the connecting tube 58 by pinching with a hemostat 160 or similar pinch-locking tool. Tube 58 is removed from tube 154 of depleted vessel. A replacement vessel 70 is provided with a connecting tube 154 on replacement bottle 70 and hemostat 160 or other pinch-locking tool is removed to reconnect fluidic circuit 130.

Figure 15:
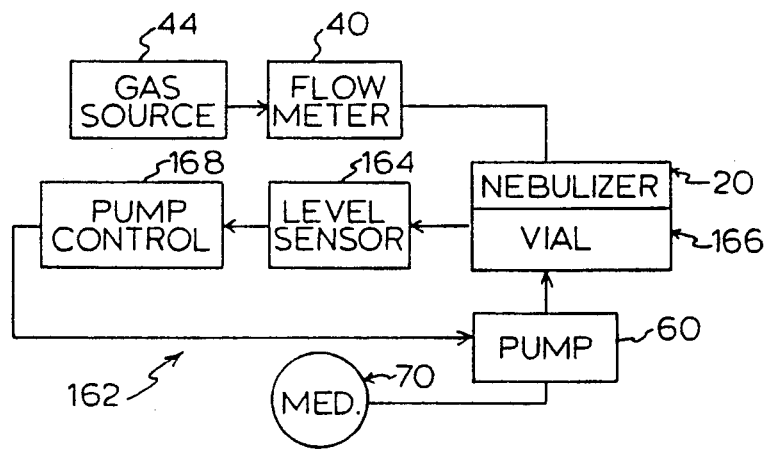
FIG. 15 is a block diagram of the parts seen in FIG. 13 attached to a nebulizer which receives gas flow from a source through a flow meter.

Another currently preferred embodiment is seen in FIGS. 14–15. The fluid supply circuit comprising pump 60 and large supply vessel 70 is the same as seen in FIG. 2, but seen only in part in FIG. 14. As pump 60 may be set to pump at rates lower or higher than effluent aerosolized flow from nebulizer 20 (as seen in FIG. 2) and it may not be desirable to return potentially contaminating fluid to large storage vessel 70, a liquid level feedback control system 162 provides underfill detection and alarm and overfill protection. As seen in FIG. 14, liquid level feedback control system 162 comprises a sensor module 164, a modified nebulizer vial 166, and a pump power control and alarm device 168 which acts to control power to pump 60.

Modified nebulizer vial 166 is similar to nebulizer vial 50 as earlier described with the exception of a plurality of flats 172 which provide windows for optical sensing of the inside of nebulizer vial 166. As seen in FIG. 15, each flat 172 is disposed in essentially vertical orientation at an inset 174 in conically shaped part 76 of nebulizer vial 166. So disposed, each flat 172 provides an optical pathway which is substantially linear relative to the depth of reservoir 72. Each flat also provides a window which extends above the maximum depth permitted for reservoir 72 and below the minimum depth permitted for reservoir 72. The plurality of flats 172, being substantially vertical and regularly disposed about the circumference of conically shaped part 76, provide a mechanically attachable surface pattern for like configured sensor module 164 which is described in detail hereafter.

Sensor module 164 comprises a bottom cross member 170 from which a plurality of fingers 176, 178, 186, and 188 vertically extend as seen in FIG. 13. Each finger 176, 178, 186, and 188 comprises a light emitting diode 180, and an inferior light sensitive diode 182, and a superior light sensitive diode 184. Each superior light sensitive diode 184 is disposed above associated light emitting diode 180 and each inferior light sensitive 182 is disposed below light emitting diode 180 such that the disposition of diodes 184 and 182 about light emitting diode 180 is symmetrical. The distance of separation of light sensitive diodes 184 and 182 is preset to determine the resolution of control of liquid level measurement. The distance may be less than one centimeter.

Finger to finger separation is predetermined to provide a snug fit of said fingers against each flat 172 of nebulizer vial 166. Thereby, a good mechanical connection is provided as well as an adequate optical coupling. Cross base 170 and fingers 176, 178, 186, and 188 may be made from rigid synthetic resinous material or from a spring metal such as beryllium copper as is well known in the art.

Electrical connections are returned from each finger 176, 178, 186, and 188 by an electrical cable 190 to pump power control and alarm device 168. Pump power control and alarm device comprises a front panel 192, an audible alarm (not shown), and a pump power connecting cable 194. Illuminating power is provided to each light emitting diode 180 in a standard manner known in the art through cable 190 from pump power control and alarm device 168. Optically sensed signals from each inferior light sensitive diode 182 and superior light sensitive diode 184 are also communicated to pump power control and alarm device 168 through cable 190.

Each associated inferior light sensitive diode 182 and superior light sensitive diode 184 comprise a sensor pair for reflectively sensing a changing optical environment inside nebulizer vial 166. Such a change occurs when the effective index of refraction changes as water or other liquid wets the inside walls of the transparent nebulizer vial 166 and thereby provides a significantly different index of refraction than air disposed thereat.

As is seen in FIG. 17, a circuit 210 measures the light differential as sampled by each light sensitive diode 182 and 184 and provides an output of a logical "one" if the differential measurement between two paired light sensitive diodes 182 and 184 is above a predetermined threshold, otherwise a logical "zero" is provided. Light emitting diode 182 is connected to a linear amplifier 196 and therefrom connected to a positive input of differential amplifier 198. Similarly, light emitting diode 184 is connected to a linear amplifier 196 and therefrom is connected to a negative input of differential amplifier 198. An output 204 of differential amplifier 198 is delivered across filtering shunt capacitor 206 to input 208 of threshold detector 200. If the differential voltage of output 204 is greater than a predetermined threshold voltage, threshold detector 200 drives output line 202 high or to a logical "one" status, representing detection of a different reflective optical environment by the associated inferior and superior light sensitive diodes 182 and 184, respectively. If no such change is sensed, the signal from threshold detector 200 maintains output line 202 low or at a logical "zero".

Referring again to FIG. 14, four fingers 176, 178, 186, and 188 are seen as used in the currently preferred embodiment. In fingers 178 and 188, light emitting diodes and associated light sensitive diodes are inferiorly disposed to measure a minimum reservoir 72 level. If a liquid-air surface is detected at the minimum level, an alarm is sounded to alert an attendant to increase pump 60 flow rate. In fingers 176 and 186, light emitting diodes and associated light sensitive diodes are superiorly disposed to measure the maximum permitted reservoir 72 level. If liquid is detected at the maximum level, the pump is turned off until the liquid is discharged, by effluent nebulization, to reduce the level of reservoir 72 below the critical level. After the reservoir is lowered below the critical level, pump 60 is turned back on to resume continuously supplying fluid to nebulizer vial 166.

Output from each associated set of sensing components in each finger 176, 178, 186, and 188 comprising a light emitting diode 180, an inferior light sensitive diode 182 and a superior light sensitive diode 184 is delivered to a circuit 210 as seen in FIG. 17. Therefore, in this currently preferred embodiment, four such circuits are provided. In such embodiment, the output 202 of circuit 210 (see FIG. 17) associated with finger 176 (see FIG. 14) is connected to circuit 232 (shown in FIG. 18) at terminal site 212. The output of circuit 202 (see FIG. 17) associated with finger 186 (see FIG. 14) is connected to circuit 232 (shown in FIG. 18) at terminal site 214. Terminal sites 212 and 214 comprise inputs to an OR gate 220, thereby providing redundancy of measurement of the maximum liquid level by fingers 176 and 186. Output line 222 of OR gate 220 bifurcates to provide input to an invertor 226 and a flip-flop set input 224. Thus, when a "one" signal occurs on either terminal sites 212 or 214, a "one" is propagated across line 222 to a set input 224, thereby setting a flip-flop 254 to a "one" state. When flip-flop 254 is set to "one", a Q-not output 230 of flip-flop 254 is transitioned to zero thereby removing power from pump 60.

When both inputs at terminal sites 212 and 214 are "zero", the "one" signal is removed from set input 224. The "zero" signal delivered to invertor 226 produces a "one" on output line 258 which is delivered to flip-flop 254 reset 228 through delay 256. Filter 256 comprises a low-pass filter adding hysteresis to reduce the frequency of turning pump 60 on and off. However, when the voltage at reset 228 is a logical "one", flip-flop 254 is reset and power is returned to pump 60.

Referring again to FIG. 18, the output of circuit 202 (see FIG. 17) associated with finger 178 (see FIG. 14) is connected to circuit 234 at terminal site 216. The output of circuit 202 (see FIG. 17) associated with finger 188 (see FIG. 14) is connected to circuit 234 at terminal site 218. Terminal sites 216 and 218 comprise inputs to an OR gate 236, thereby providing redundancy of measurement of the minimum liquid level by fingers 178 and 188 (see FIG. 14). Output line 238 of OR gate 236 provides an input to a set input 242 of flip-flop 240. Thus, when a "one" signal occurs on either terminal sites 216 or 218, a "one" is propagated across line 238 to set input 242 of flip-flop 240. When flip-flop 240 is set, a Q output 246 of flip-flop 240 transitions to "one" thereby turning on an alarm light 250 seen in FIG. 14 on the control panel 192 of pump power control and alarm device 168 and an audible alarm as well. The alarm is reset by a manual reset switch 248 disposed and available for manual control on the control panel of pump power control and alarm device 168.

Such components and circuits as used in this currently preferred embodiment and seen in FIGS. 17 and 18 are known and widely available in the art.

Reference is now made to FIG. 15 which comprises a block diagram of the electro-fluidic circuit for the embodiment seen in FIG. 14. Therein feedback circuit 162 comprises pump 60, nebulizer vial 166, sensor module 164, and pump power control and alarm device 168. Large supply vessel 70 provides liquid for pump 60.

Figure 16:
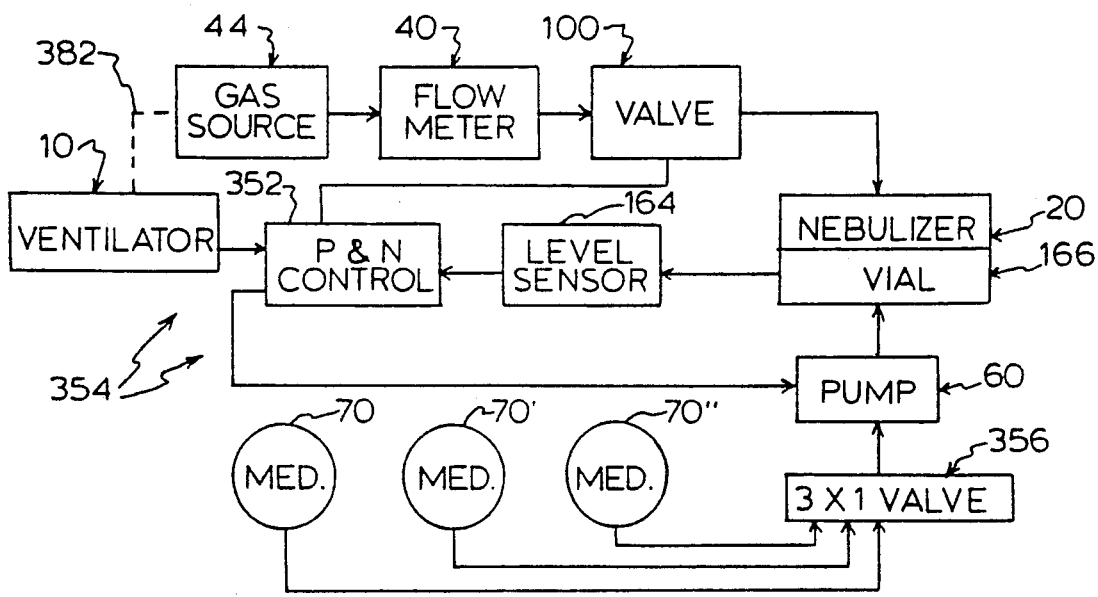
FIG. 16 is a block diagram of a continuous flow, multiple medication deivery system comprising a plurality of large storage vessels, a manual selection valve disposed between the vessel and a single pump, the pump, a liquid level sensor, a ventilator, and ventilator control applied to a mode selecting valve for synchronization of flow of nebulizing gas with selected portions of the cycle of the ventilator.

Another currently preferred embodiment is seen in FIG. 16. FIG. 16 is a block diagram of a control circuit 354 comprising increased complexity over circuit 162 of FIG. 15. Control circuit 354 comprises a plurality of large supply vessels 70, 70', and 70" and a pump and nebulizer controller 352. In addition, control circuit 354 comprises a ventilator 10 input to pump and nebulizer controller 352 whereby modes of control are selected for operation of valve 100 to provide the frequency and periodicity of nebulizing gas represented by options 1–4 in FIG. 10. A valve 356 provides for manual selection of any one of the contents of large supply vessels 70, 70', 70" to be delivered by pump 60 to nebulizer vial 166. As sensor module 164 and pump power control and alarm device 168 controls pump 60 and alarms in circuit 162, pump and nebulizer controller 352 controls pump 60 and alarms in circuit 354. Thus, this currently preferred embodiment provides selective control of fluid flow from a plurality of large supply vessels 70, 70', and 70", provides optional modes of control of nebulizer operational modes by valve 100, and liquid level sensing by sensor module 164 under control of pump and nebulizer controller 352. In those cases where a significant portion of respiratory flow to patient 30 flows into the nebulizing gas introducing nozzles of the nebulizer, it is important that the same mix of gases be provided to gas source 44 as is provided to patient 30 through normal respiratory channels. In such a case, ventilator 10 gas is provided to gas source 44 through a flow connecting tube seen as a dashed line 382 in FIG. 16.

Figures 19, 21:
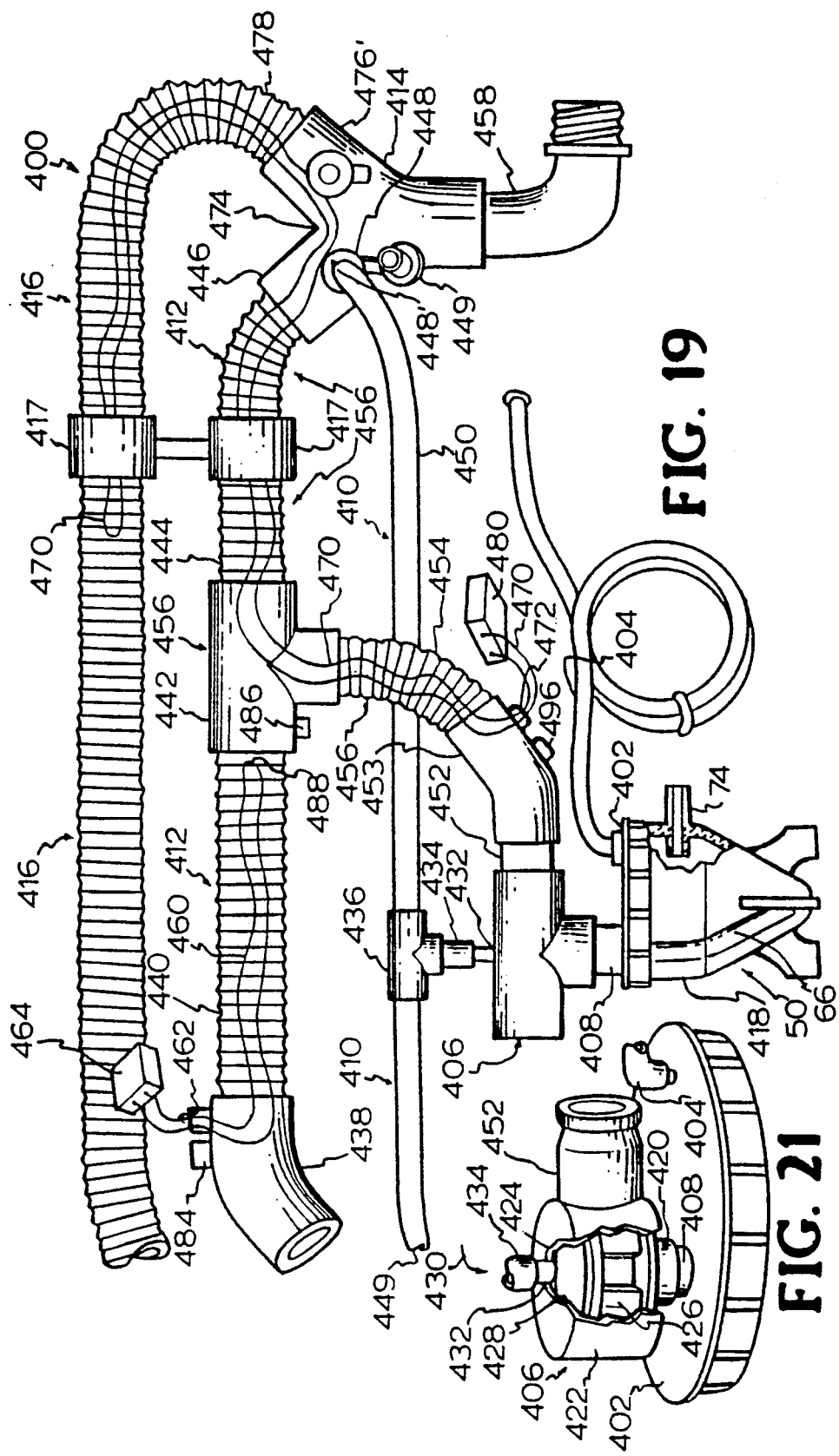
FIG. 19 is a perspective of an apparatus which provides intermittent flow control and temperature control of ventilator output, nebulizeable and nebulized fluids prior to delivery to the patient.
FIG. 21 is a segmented perspective of a fluidic control valve seen in the apparatus of FIG. 19 with parts removed for clarity of presentation.

Another currently preferred embodiment of the invention comprising nebulizeable fluid, nebulized fluid and inspired fluid temperature controls is seen in FIGS. 19–22. An apparatus 400 which provides continuously replenished, temperature controlled nebulizeable fluids to nebulizer vial 50 is seen in FIG. 19. Beginning at nebulizer vial 50, apparatus 400 comprises a nebulizer 402 which connects to nebulizer vial 50, gas source connecting tubing 404 connected to the nebulizer 402, and nebulized fluid valve 406 connected to an output discharge shaft 408 of nebulizer 402. Further, apparatus 200 comprises a pressure feedback tubing 410 and inhalation pathway tubing 412, a "Y" connector 414, exhalation gas pathway tubing 416, and an inhalation and exhalation tubing coupling connector 417.

As seen in FIG. 19, feedthrough 74 is disposed in a vertical ring 418 of nebulizer vial 50 which is disposed below the connection of nebulizer vial 50 and nebulizer 402. As earlier described, tube 66 draws fluid from reservoir 72, seen in FIG. 20, in nebulizer vial 50 into nebulizer 402 where nebulization takes place dispensing the gas product superiorly into vertical shaft 408.

Vertical shaft 408 is inferiorly disposed beneath nebulized fluid valve 406 where a releasibly sealed connection is made providing a pathway for discharging nebulized fluid. Fluid valve 406 comprises a single moving part, a normally open mechanical valve leaf 424, best seen in FIG. 21, which operates fluidically to control discharge of fluidized liquid from nebulizer 402.

As seen in FIG. 21, ascending fluid flow, upward out of nebulizer 402 and through shaft 408 is valvularly controlled by valve 406. Valve 406 comprises an inferiorly disposed stem 420 by which a releasibly sealed connection is made to shaft 408. Stem 420 is elongated into valve body 422 where an abutting contact (not shown) is made against a pliant mechanical valve leaf 424. Valve leaf 424 is disposed above shaft 408, stem 420, supporting structure 426 such that a sealed chamber 428 is defined for fluid which passes into chamber 428 through a pathway indicated by arrow 430 defined by a superiorly, centrally disposed orifice and tube connecting stem at site 432 and a tube 434. Tube 434 connects through a "T" connector 436 which is interposed between divided tube 410 which connects on one end 448" to a ventilator 10 manometer connection 448 in "Y" connector 414 such that the inhalation pressure in "Y" connector 414 is fed back to valve 406. Note that manometer connection 448 comprises a tethered plug 449 which caps manometer connection 448 to provide a seal when tube 410 is disconnected. As the manometer pressure is also used as a control variable in ventilator 10, the other free end 449 of tube 410 provides the manometer pressure feedback input to ventilator 10.

Inspiratory flow to the lungs of the patient 30 is provided from ventilator 10 through elbow 438, ventilatory tube section 440, ventilation connecting "T" 442, ventilatory tube section 444 to "Y" connector 414 influent flow receiving member 446. When inspiratory flow occurs, the concurrent rise in pressure in receiving member 446 is fed back through the sampling port of manometer connection 448 through connecting tube segment 450 of tube 410, connecting "T" 436 and tube 434 to chamber 428 of valve 406. Inspiratory flow pressure thereby increases the pressure in chamber 428 which is thereby exerted upon valve leaf 424 to close valve 406 and terminate flow therethrough.

At the end of each inspiration cycle, influent flow and the associated pressure is removed from the inspiratory pathway of elbow 438, ventilation connecting "T" 442, aand influent flow member 446, thereby reducing the pressure in manometer pressure carrying tube 410. Subsequently, the same pressure drop occurs in chamber 428, which causes valve 406 to open. Release of pressure upon valve leaf 424 opens a pathway out of valve 406 through an outlet port 452. Outlet port 452 is connected through elbow 453 to a ventilatory tube 454 and from there to ventilation connecting "T" 442 wherein the flow from nebulizer 402 merges with fluid in the inspiratory pathway comprising ventilating tube segments 440 and 444.

So connected, nebulizeable fluid is received from a remote source of nebulizeable medicant as described hereinabove and deposited into a reservoir 72 in nebulizer vial 50 as seen in FIG. 20. The nebulizeable fluid is drawn into nebulizer 402 through tube 66 and nebulized thereat. Nebulized fluid courses through shaft 408 and flows through valve 406 during each exhalation cycle. As nebulized fluid is displaced into an otherwise nonflowing fluid space during expiration, mixing occurs with the other fluid in the reservoir 456 provided by the space comprising tube 454, ventilation connecting "T" 442 and tube segment 444. During inspiration cycle, at least a portion of the fluid residing in reservoir 456 is swept through the "Y" connector 414 to the pathway leading via an endotracheal tube connector 458 to the lungs of the patient 30 (not seen in FIGS. 19 and 20).

It is often medically more efficacious and safer to provide inspiratory fluid at a predetermined temperature which is different than an otherwise uncontrolled temperature of the mixed fluid temperature from ventilator 10 and nebulizer 402. For this reason, in-line heating wires are provided as seen in FIGS. 19 and 20. A first heating wire 460 is provided through a sealed entry port 462 provided in elbow 438. First heating wire 460 is used to pre-heat fluid flowing from ventilator 10. First heating wire 460 comprises a single loop of wire which enters elbow 438 and extends through tube segment 440 substantially to the connection of tube segment 440 with ventilation connecting "T" 442. The distal ends of first heating wire 460 terminate in a connector 464 which, when used, is joined to a mating connector 446 as best seen in FIG. 20. Mating connector 466 provides input to a temperature regulator 468, the function of which is described in detail hereinafter.

A second heating wire 470 is sealably inserted into the nebulizing fluid pathway via a port 472 in elbow 453 as first heating wire 460 is inserted into port 462. Similar to first heating wire 460, second heating wire 470 comprises a single loop of wire. Second heating wire 470 extends from port 472 through ventilation connecting "T" 442, tube segment 444, and influent member 446. At a "Y" junction of "Y" connector 414, second heating wire 470 is fed into the exhalation pathway comprising an effluent member 476' and an exhalation ventilatory tube segment 478 of exhalation gas pathway 416. So disposed, the second heating wire 470 heats influent fluid flowing into the lungs of patient 30 and effluent fluid exiting the lungs of patient 30.

Component parts used for controlling temperature are better seen in FIG. 20. Temperature control for the first heating wire 460 comprises the first heating wire 460 and associated connectors 464 and 466, a low temperature sensing probe 478, and temperature regulator 468. Low temperature sensing probe 476 is disposed as a sealed plug in probe site 484 in elbow 438 upstream from first heating element entry port 462. The high temperature sensing probe 478 is disposed as another sealed plug in probe site 486 in ventilation connecting "T" 442 which is downstream from the end 488 of first heating wire 460.

Temperature regulators and associated parts comprising a low temperature probe and a high temperature probe and power providing drivers for heating a single loop of wire are well know and widely used in the art. Such temperature regulators comprise controls permitting setting predetermined temperatures about which the temperature is regulated.

Component parts for controlling the second heating wire 470 comprises the second heating wire 470 and associated connectors 480 and 482, a lower temperature sensing probe 490, a higher temperature sensing probe 492, and temperature regulator 494. Temperature regulator 494 is essentially the same as temperature regulator 468. As seen in FIG. 20, connectors 480 and 482 are disconnected to demonstrate the use of a reusable part such as temperature regulator 494 with a part which may be disposable such as apparatus 400.

Lower temperature sensing probe 490 is disposed at a probe site 496 in elbow 453 between port 472 where second heating wire enters the nebulized fluid flow path and valve 406 which is upstream from elbow 453. Higher temperature sensing probe 492 is disposed at probe entry 498 disposed in effluent member 476'. Disposition of probe entry site 498 in effluent member 476' permits measurement of the temperature of fluid heated by the second heating wire 470 at a site where the temperature of influent and effluent fluid from patient 30 is sensed.

In some cases it is more efficacious to controllably adjust the temperature of medicant prior to aerosolization thereof. As seen in FIG. 20, a third temperature regulator is provided to thermally prepare nebulizeable fluid for aerosolization. Temperature regulator 500 is disposed between pump 60 and large supply vessel 70. Large supply vessel 70 is connected to temperature regulator 500 via tube 58. Output from temperature regulator 500 flows to pump 60 through a tube 58', and pump 60 is connected to feedthrough 74 of nebulizer vial 50 through tube 54. Thus, nebulizeable fluid from large supply vessel 70 is drawn through temperature regulator 500 while being transported to reservoir 72.

While the temperature of nebulizeable fluid may be regulated to any predetermined and desired temperature dependent upon the characteristics of the medicant being employed, temperature regulator 500 in this currently preferred embodiment comprises a tubing coil 502 immersed in an ice bath 504 in a container 506, as best seen in FIG. 22. Container 506 comprises an inlet port 508 and an outlet port 510 which communicate with the influent and effluent ends of tubing coil 502. A stop cock 512 is placed at each inlet port 508 and outlet port 510 for use during maintenance and servicing of temperature regulator 500. Tubing coil 502 is of sufficient length to reduce the temperature of the nebulizeable fluid to substantially the temperature of the ice bath 504 during continuous operation.

Referring again to FIG. 20, nebulizing gas is provided from gas source 44 to flow to adjusting flow meter 40 through tubing 42'. Metered gas flows from flow meter 40 to nebulizer 402 through tubing 404 in the direction indicated by dashed arrows 26'. Concurrent with metered flow from flow meter 40, nebulizeable fluid is drawn from large supply vessel 70 through tube 58 in the direction of dashed arrows 56" to temperature regulator 500. Pump 60 draws temperature regulated fluid from temperature regulator 500 at a metered rate which is substantially the same as the nebulizing rate of nebulizer 402.

Fluid flows from pump 60 into reservoir 72 of nebulizing vial 50 through tube 54 in the direction of dashed arrows 56'. Nebulizeable fluid is drawn from reservoir 72 in nebulizer 402 through tube 66. A mixture of nebulized fluid and nebulizing gas from gas source 44 is discharged into output shaft 408 which is connected to valve 406 as earlier described.

Valve 406 opens to permit discharge of the mixture into outlet port 452 when the manometer pressure at manometer connection 448 indicates the exhalation portion of a respiratory cycle is in progress. Manometer pressure is provided through a bifurcation in manometer pressure sampling tube 410 which provides manometer pressure feedback to ventilator 10 along the path indicated by dashed line 451. During exhalation, respiratory gas from patient 30 is returned through effluent member 476' and ventilatory tubing pathway 416 along a path indicated by dashed arrows 28' to ventilator 10. Flow from valve 406, exiting through port 452, is discharged to travel along a path as indicated by dashed lines 512 and 514 to mix the fluid contained in a reservoir defined by tubing 454, ventilation connecting "T" 442 and tube segment 444 such that, upon initiation of the inhalation portion of the respiratory cycle, the mixture is delivered to the lungs of patient 30.

Influent respiratory gas is provided from ventilator 10 through ventilatory tube segment 516, elbow 438, and tube segment 440 to flow to conjoining ventilation connecting "T" 442 in the direction indicated by dashed arrows 26'. The temperature of influent gas from ventilator 10 and the mixture of gas which is initiated at ventilation connecting "T" 442 is regulated as earlier described such that influent gas entering endotracheal connector 458 is at a predetermined temperature. Endotracheal connector 458 accomodates di-directional flow as indicated by arrow 520. Influent flow to the lungs of patient 30 arrives at the endotracheal tube via influent member 446. Effluent flow from the lungs of the patient 30 departs through effluent member 476'.

The invention may be embodied in other specific forms without departing from the spirit or essential characteristics thereof. The present embodiments are therefore to be considered in all respects as illustrative and not restriction, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. An apparatus for delivering an aerosolized medication to a patient for administration, comprising:
   (a) a non-ultrasonic nebulizer assembly, comprising:
      (i) a nebulizer vial including a vertically extending housing comprising at least one side wall and defining a reservoir for holding liquid medication therein in a volume defining a gas-liquid interface within the housing;
      (ii) a nebulization mechanism constructed and arranged to effect gas-liquid contacting of gas with liquid medication from the volume of liquid medication held in the reservoir, and produce said aerosolized medication;
      (iii) a liquid medication feed passage member extending transversely through a side wall of said vertically extending housing for transverse introduction of liquid medication into the reservoir, said liquid medication feed passage member being disposed at an elevation above the gas-liquid interface defined by liquid medication held in the reservoir; and
      (iv) a gas feed passage member for feeding gas to the nebulization mechanism;
   (b) means for supplying gas to the nebulizer assembly including the gas feed passage member thereof;
   (c) means for monitoring the rate of flow of gas supplied to the gas feed passage member of the nebulizer assembly;
   (d) means for discharging aerosolized medication from the nebulizer assembly and delivering same to a patient for administration;
   (e) a supply vessel for containing a source volume of the liquid medication wherein said source volume is greater than the volume of liquid medication held in said reservoir of said nebulizer vial;
   (f) a liquid medication flow circuit interconnecting said supply and said liquid medication feed passage member, for flowing liquid medication from the supply vessel to the liquid medication feed passage member for introduction of liquid medication into the reservoir; and
   (g) liquid medication flow control means disposed in said liquid medication flow circuit for controlling the flow rate of liquid medication from the supply vessel to the liquid medication feed passage member during operation of said treatment apparatus involving delivery of aerosolized medication to a patient for administration, and arranged for controlling the flow rate of liquid medication from the supply vessel to the liquid medication feed passage member, with respect to the rate of flow of gas supplied to the nebulizer assembly, and in accordance with a nomogramic relationship between the flow rate of gas and the flow rate of liquid medication. the liquid medication flow control means controlling the flow rate of liquid medication from the supply vessel to the liquid medication feed passage member to be substantially equal to the rate of loss of liquid medication from the reservoir in the aerosolized medication discharged from the nebulizer assembly and delivered to the patient for administration and continuously maintaining the gas-liquid interface at a selected position and continuously maintaining a constant volume of liquid medication in the reservoir of the nebulizer vial during said operation.

2. An apparatus according to claim 1, wherein the nebulizer vial has a cylindrical-shaped upper part and a generally conical-shaped lower part joined thereto.

3. An apparatus according to claim 1, wherein the nebulization mechanism comprises means for entraining liquid medication, from the volume of liquid medication held in the reservoir, in a carrier gas to produce said aerosolized medication.

4. An apparatus according to claim 3, wherein the nebulization mechanism further comprises means for dispersing liquid medication entrained in said carrier gas.

5. An apparatus according to claim 1, wherein the nebulization mechanism comprises:
   (A) a nozzle which is constructed and arranged for connection to a source of gas, to discharge a gas stream as nebulization carrier gas; and
   (B) a generally downwardly extending aspiration tube having (i) a lower inlet end disposed in a lower portion of the housing at an elevation below the gas-liquid interface defined by liquid medication held in the reservoir, and (ii) an upper part including an aspiration port in liquid aspiration relationship to the nozzle, for aspiratingly flowing liquid medication through the aspiration tube, from the lower inlet end, when in liquid flow communication with the volume of liquid medication in the reservoir of the nebulizer vial during said operation, to said aspiration port for entrainment in the gas stream discharged from the nozzle as nebulization carrier gas.

6. Apparatus according to claim 5, wherein the nebulization mechanism further comprises a baffle plate in impingement relationship to the gas stream discharged from the nozzle as nebulization carrier gas, whereby liquid medication entrained in the nebulization carrier gas is impacted against the baffle plate to enhance aerosolization thereof.

7. Apparatus according to claim 1, wherein the liquid medication flow control means (g) comprise a variable rate pump.

8. Apparatus according to claim 1, wherein the liquid medication flow control means (g) comprises a syringe infusion pump.

9. Apparatus according to claim 1, wherein the liquid medication feed passage member extending transversely through the side wall of the vertically extending housing is devoid of any flow restriction means therein.

10. Apparatus according to claim 1, wherein the liquid medication feed passage member is generally perpendicular to the side wall of the vertically extending housing.

11. Apparatus according to claim 1, wherein the liquid medication feed passage member and the flow circuit interconnecting the supply vessel and the feed passage member are devoid of any check valve or directional flow restriction means therein.

12. An apparatus according to claim 1, wherein the nebulization mechanism comprises a means for effecting aspiration of liquid medication onto a baffle surface to effect the dispersion into droplets of the liquid medication.

13. An apparatus according to claim 1, wherein the liquid medication feed passage member extending transversely through a side wall of the vertically extending nebulizer vial housing has a terminus at said side wall.

14. An apparatus for delivering an aerosolized medication from a nebulizer containing a volume of liquid medication to a patient for administration, comprising:
  (a) a nebulizer assembly, comprising:
    (i) a nebulizer vial including a vertically extending housing comprising at least one side wall and defining a reservoir for holding therein a volume of liquid medication defining a gas-liquid interface within the housing,
    (ii) a nebulization mechanism constructed and arranged to effect gas-liquid contacting of gas with liquid medication from the volume of liquid medication held in the reservoir, and produce said aerosolized medication; and
    (iii) a feed passage member extending transversely through a side wall of said vertically extending housing for transverse introduction of liquid medication into the reservoir, said feed passage member being disposed at an elevation above the gas-liquid interface defined by liquid medication held in the reservoir;
  (b) a supply vessel for containing a source volume of the liquid medication within said source volume which is greater than the volume of liquid medication held in said reservoir of said nebulizer vial;
  (c) a flow circuit interconnecting said supply vessel and said feed passage member, for flowing liquid medication from the supply vessel to the feed passage member for introduction of liquid medication into the reservoir;
  (d) flow control means disposed in said flow circuit for controlling flow rate of liquid medication from the supply vessel to the feed passage member during operation of said treatment apparatus involving delivery of aerosolized medication to a patient for administration, to continuously maintain the gas-liquid interface at a selected position and to continuously maintain a constant volume of liquid medication in the reservoir of the nebulizer vial during said operation; and
  (e) means for discharging aerosolized medication from the nebulizer assembly when delivering same to said patient for administration;
  wherein:
  said nebulization mechanism is constructed and arranged to provide a selected effluent rate of aerosolization of liquid medication from said reservoir, as discharged by said aerosolized medication discharging means (e) from the nebulizer assembly;
  said nebulizer assembly comprises an overflow passage member extending through said vertically extending housing in liquid flow communication with the volume of liquid medication;
  said flow circuit (c) is part of a fluidic closed loop comprising a second flow circuit interconnecting said supply vessel and said overflow passage member exteriorly of said housing; and
  said flow control means (d) comprise a pump which is constructed and arranged to provide a flow rate of liquid medication from the supply vessel to the feed passage member which is higher than said effluent rate of aerosolization from the nebulization mechanism (a)(ii);
  whereby the gas-liquid interface is continuously maintained at said selected position and said constant volume of liquid medication is continuously maintained in the reservoir of the nebulizer vial following said operation.

15. An apparatus for delivering an aerosolized medication to a patient for administration, comprising:
  (a) a nebulizer assembly comprising:
    (i) a nebulizer vial including a vertically extending housing comprising at least one side wall and defining a reservoir for holding liquid medication therein in a volume defining a gas-liquid interface within the housing;
    (ii) a nebulization mechanism constructed and arranged to effect gas-liquid contacting of gas with liquid medication from the volume of liquid medication held in the reservoir, and produce said aerosolized medication;
    (iii) a liquid medication feed passage member extending transversely through a side wall of said vertically extending housing for transverse introduction of liquid medication into the reservoir, said liquid medication feed passage member being disposed at an elevation above the gas-liquid interface defined by liquid medication held in the reservoir; and
    (iv) a gas feed passage member for feeding gas to the nebulization mechanism;
  (b) means for supplying gas to the nebulizer assembly including the gas feed passage member thereof;
  (c) means for monitoring the rate of flow gas supplied to the gas feed passage member of the nebulizer assembly;
  (d) means for discharging aerosolized medication from the nebulizer assembly and delivering same to a patient for administration;
  (e) a supply vessel for containing a source volume of the liquid medication wherein said source volume is greater than the volume of liquid medication held in said reservoir of said nebulizer vial;
  (f) a liquid medication flow circuit interconnecting said supply vessel and said liquid medication feed passage member, for flowing liquid medication from the supply vessel to the liquid medication feed passage member for introduction of liquid medication into the reservoir; and
  (g) liquid medication flow control means disposed in said liquid medication flow circuit for controlling the flow rate of liquid medication from the supply vessel to the liquid medication feed passage member during operation of said treatment apparatus involving delivery of aerosolized medication to a patient for administration, and arranged for controlling the flow rate of liquid medication from the supply vessel to the liquid medication feed passage member, with respect to the rate of flow of gas supplied to the nebulizer assembly, and in accordance with a nomogramic relationship between the flow rate of gas and the flow rate of liquid medication the liquid medication flow control means controlling the flow rate of liquid medication from the supply vessel to the liquid medication feed passage member to be substantially equal to the rate of loss of liquid medication from the reservoir in the aerosolized medication discharged from the nebulizer assembly and delivered to the patient.

* * * * *